(12) United States Patent
Aurora et al.

(10) Patent No.: US 10,328,123 B2
(45) Date of Patent: *Jun. 25, 2019

(54) PULSED INTRODUCTION OF LOW-DOSE RANKL AS A THERAPY FOR ATHEROSCLEROSIS

(71) Applicant: St. Louis University, St. Louis, MO (US)

(72) Inventors: Rajeev Aurora, Wildwood, MO (US); Anna Smith, St. Peters, MO (US); Angel Baldan, St. Louis, MO (US)

(73) Assignee: Saint Louis University, St. Louis, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/659,570

(22) Filed: Jul. 25, 2017

(65) Prior Publication Data

US 2018/0085431 A1    Mar. 29, 2018

Related U.S. Application Data

(63) Continuation-in-part of application No. 15/052,793, filed on Feb. 24, 2016, now Pat. No. 9,713,633, and a continuation-in-part of application No. 15/265,540, filed on Sep. 14, 2016, which is a continuation-in-part of application No. 15/052,793, filed on Feb. 24, 2016, now Pat. No. 9,713,633.

(60) Provisional application No. 62/120,753, filed on Feb. 25, 2015, provisional application No. 62/120,753, filed on Feb. 25, 2015.

(51) Int. Cl.
*A61K 38/17* (2006.01)

(52) U.S. Cl.
CPC .................................. *A61K 38/177* (2013.01)

(58) Field of Classification Search
None
See application file for complete search history.

(56) References Cited

U.S. PATENT DOCUMENTS

| | | | |
|---|---|---|---|
| 7,364,736 | B2 | 4/2008 | Boyle et al. |
| 2009/0162426 | A1* | 6/2009 | Penninger ............. A61K 31/00 424/450 |

OTHER PUBLICATIONS

Rohm et al., Mediators Inflamm. 2015:364710. (Year: 2015).*
Montecucco et al., Clin Dev Innnnunol.2007:75805: (Year: 2007).*
Choi et al., Eur J Clin Invest. Apr. 2008;38(4):211-217 (Year: 2008).*
Cline-Smith et al., "Pulsed low-dose RANKL as a potential therapeutic for postmenopausal osteoporosis," JCI Insight 2016; 1(13); e88839; doi:10.1172/jci.insight.88839, downloaded from http://insight.jci.org on Aug. 18, 2016; http://dx.doi.org/10.1172/jci.insight.88839 (11 pages).
Kiesel et al., "Cross-Presentation by Osteoclasts Induces FoxP3 in CD8 + T Cells," The Journal of Immunology 2009; 182: 5477-5487; doi: 10.4049/jimmunol.0803897, http://www.jimmunol.org/content/182/9/5477, downloaded on Dec. 3, 2014 (12 pages).
Marini et al., "Osteogenesis Imperfecta," Endotext, http://www.endotext.org/chapter/osteogenesis-imperfecta/?singlepage=true, downloaded on Aug. 30, 2016, printed on Dec. 9, 2016 (37 pages).
Forlino et al., "Osteogenesis imperfecta," Lancet 2016; 387: 1657-1671, www.thelancet.com, published online Nov. 3, 2015, http://dx.doi.org/10.1016/S0140-6736(15)00728-X (15 pages).

* cited by examiner

*Primary Examiner* — Daniel C Gamett
(74) *Attorney, Agent, or Firm* — Lewis Rice LLC

(57) ABSTRACT

Systems and methods for inhibiting atherosclerosis using FoxP3+ CD8 T-cells ($Tc_{REG}$). Osteoclasts are induced to produce FoxP3+ CD8 T-cells ($Tc_{REG}$) through introduction of a low-dose of a RANK agonist suck as RANKL. The RANKL was found to best work when provided in accordance with a schedule resulting in a pulsed administration.

7 Claims, 19 Drawing Sheets

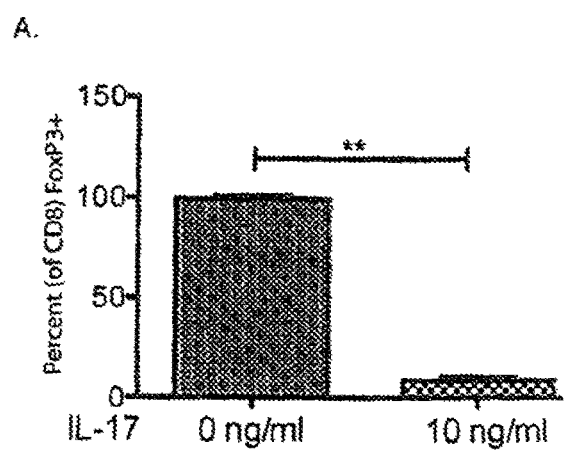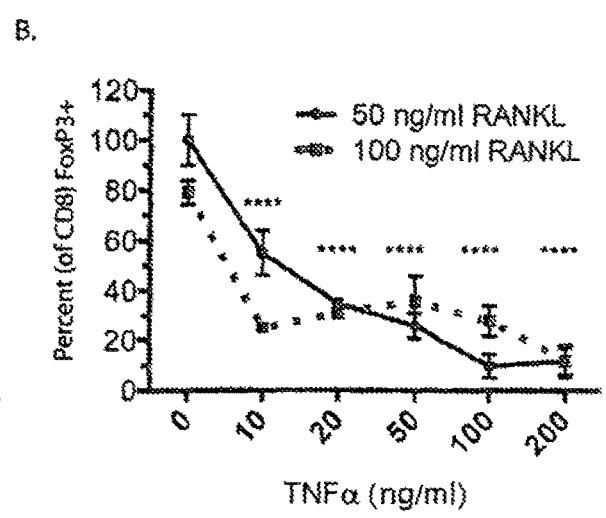
FIG. 3A
FIG. 3B

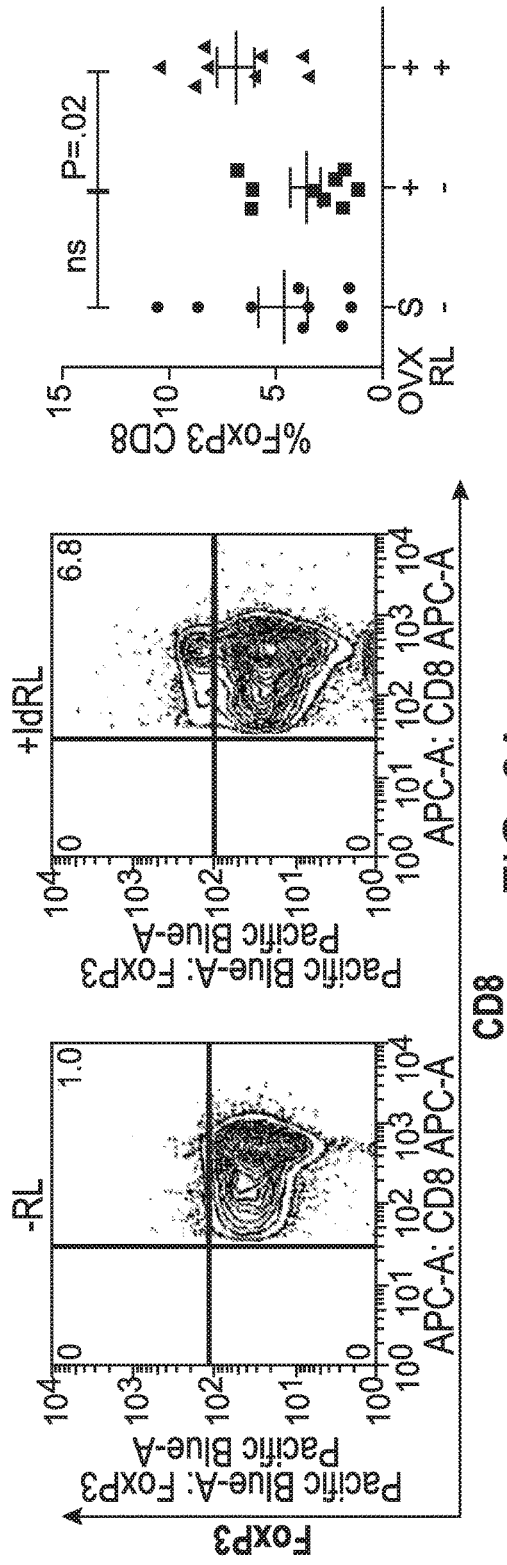
FIG. 6A
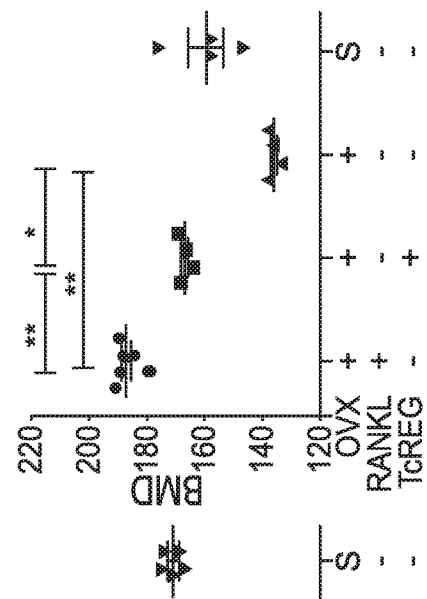
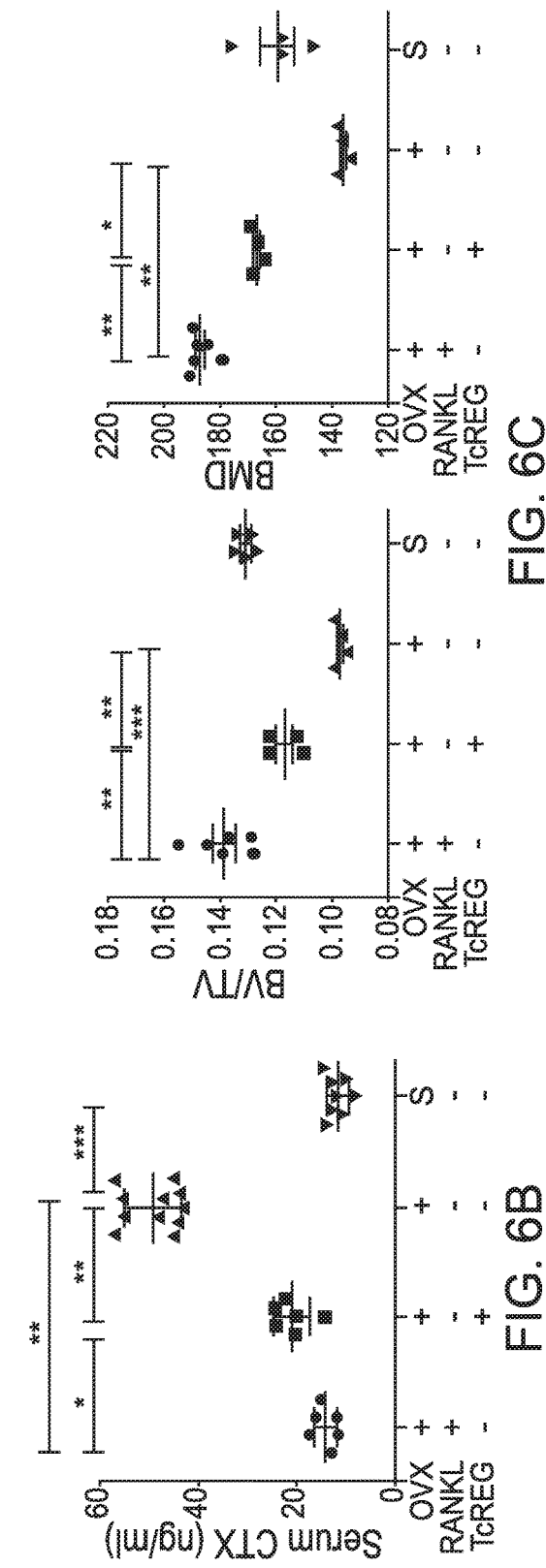
FIG. 6B
FIG. 6C

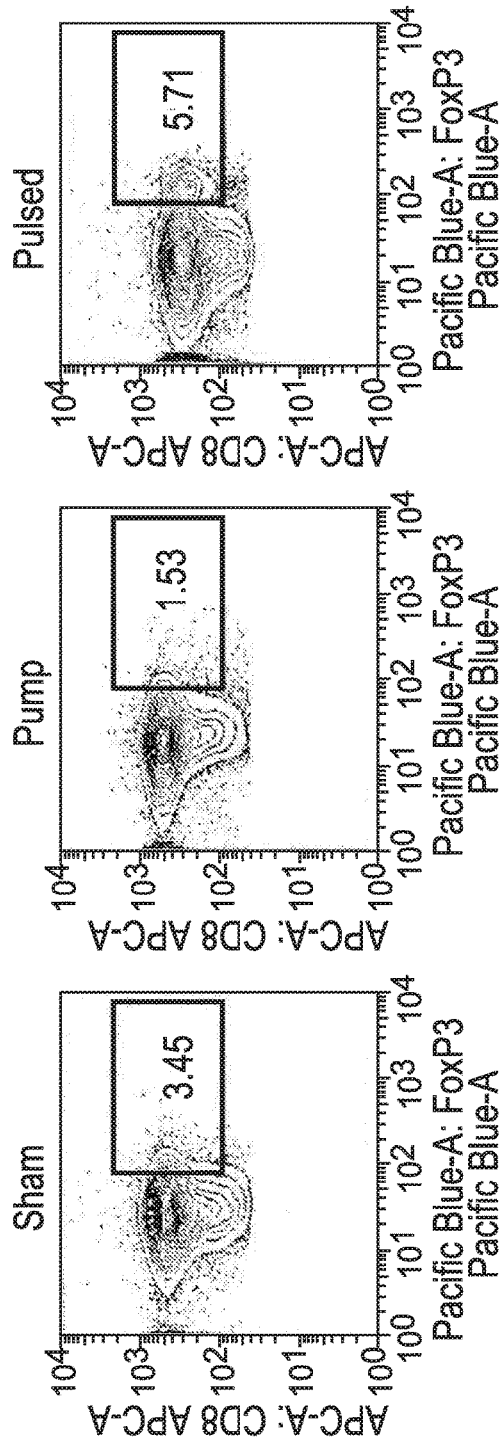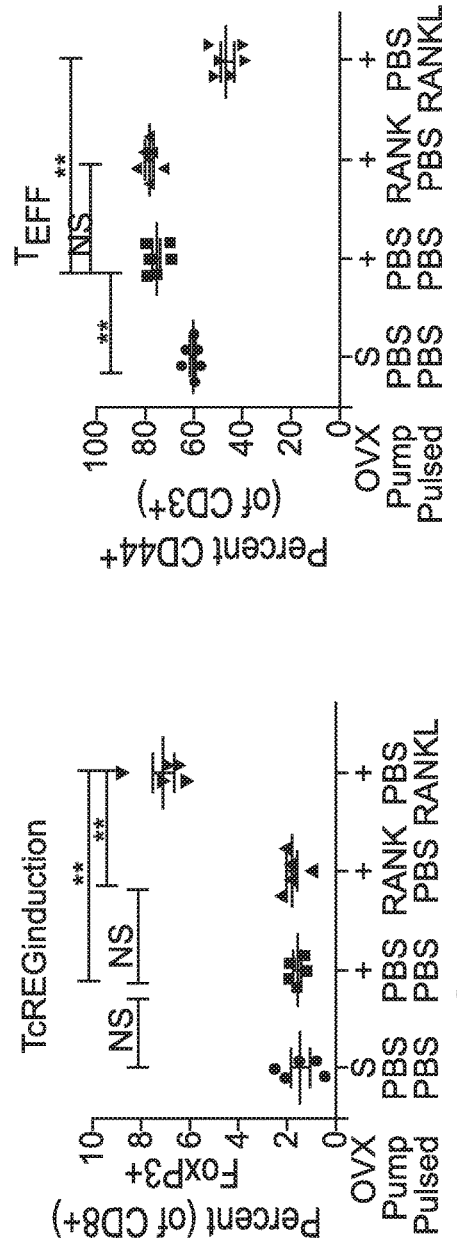
FIG. 10A
FIG. 10B
FIG. 10C

PULSED INTRODUCTION OF LOW-DOSE RANKL AS A THERAPY FOR ATHEROSCLEROSIS

CROSS REFERENCE TO RELATED APPLICATIONS

This Application is a Continuation-In-Part (CIP) of U.S. patent application Ser. No. 15/052,793, filed Feb. 24, 2016 and currently pending, which in turn claims the benefit of U.S. Provisional Patent Application Ser. No. 62/120,753, filed Feb. 25, 2015. This Application is also a Continuation-In-Part (CIP) of U.S. patent application Ser. No. 15/265,540, filed Sep. 14, 2016, which is turn is a Continuation-In-Part (CIP) of U.S. patent application Ser. No. 15/052,793, filed Feb. 24, 2016, and claims the benefit of U.S. Provisional Patent Application Ser. No. 62/120,753, filed Feb. 25, 2015. The entire disclosure of all the above documents is incorporated herein by reference.

BACKGROUND OF THE INVENTION

1. Field of the Invention

This disclosure is related to the field of devices, methods, treatments and processes for atherosclerosis. Specifically, this disclosure relates to the use of low-dose pulsed RANKL can be used as a therapy for atherosclerosis.

2. Description of Related Art

The human skeletal system is a dynamic system—an individual's bone structure is constantly being remodeled. Bone consists of a protein matrix embedded in a mineral layer. Two cells play a key role in the ever-changing reconstruction of an individual's bone structure throughout his or her life: osteoclasts and osteoblasts. Osteoclasts are large multinucleated cells that are the principal, if not sole, bone resorbing cells in the body. Stated differently, and simply, osteoclasts are cells that remove bone tissue from the skeletal system through bone resorption; i.e., by removing and breaking up a bone's mineralized matrix. Osteoblasts, which are the cells responsible for bone formation, balance the function of osteoclasts. The activity of osteoblasts is regulated by several growth factors, including transforming growth factor beta and bone morphogenetic protein. Osteoblasts, in turn, regulate the production of osteoclasts by secreting macrophage colony stimulating factor (M-CSF) and displaying the receptor activator of NF-κB ligand (RANKL) on their cell surface to induce cells of the monocytic/macrophage lineage to develop into osteoclasts.

In healthy organisms, the two cells operate in homeostasis with the amount of bone resorption, and formation, being in harmony. Alteration of the carefully balanced roles of osteoclasts and osteoblasts in this dynamic system can result in the creation of certain problematic conditions. For example, increased activity of osteoblasts, but more commonly the decreased activity of osteoclasts, leads to osteoporosis, where the bones become overly dense leading to stress factures. In contrast, increased activity of osteoclasts or decreased activity of osteoblasts, leads to bone deconstruction which can manifest itself in osteoporosis and Paget's disease, which result in bones being fragile and brittle.

Recently, it has been discovered that the equilibrium of the skeletal system, skeletal homeostasis, does not operate in a vacuum but, rather, is dynamically influenced by the human immune system. For example, lymphocyte-derived cytokines, such as the receptor activator of NF-kB ligand (RANKL), interleukin (IL)-17 and type I and II interferons, are potent mediators of osteoclast function and osteoclastogenesis. Further, osteoclast activity and numbers are increased by cytokines produced by pro-inflammatory effector T-cells, augmentation of which leads to the bone erosion which occurs in inflammatory diseases such as rheumatoid arthritis and periodontitis. T-cell produced cytokines also play a critical role in bone cancers, post-menopausal osteoporosis, and in Paget's disease. This crosstalk between the immune and skeletal system has been termed osteoimmunology.

Currently, one way in which inflammation and bone-loss-based diseases, such as but not limited to osteoporosis, rheumatoid arthritis, periodontitis, Paget's disease and bone cancers, are treated is through multiple classes of anti-inflammatory agents including nonsteroidal anti-inflammatory agents/analgesics (NSAIDs), steroids and biologics that mediate the TNFα blockade. These forms of treatment address the effects of the disease; i.e., reducing inflammation, but do not directly counteract the underlying bone loss. Generally, these forms of treatment are effective in about 30-50% of patients. However, each of these classes of anti-inflammatory agents also have severe safety and adverse reaction issues, which tend to limit their use in specific populations.

Another treatment methodology for inflammatory and bone-loss-based diseases are drugs or biologics which directly treat osteoporosis and bone erosion. For example, bisphosphonates (also called diphosphonates) are a widely-prescribed class of drugs that prevent the loss of bone mass by inhibiting the digestion of bone though encouraging osteoclasts to undergo apoptosis, or cell death, thereby slowing bone loss. However, use of bisphosphonates comes with serious safety issues. First, osteonecrosis of the jaw is increased in patients taking bisphosphonates. Second, even though bisphosphonates slow bone loss, the risk of bone fracture in elderly patients is increased in patients on this class of drugs. This increase is most likely due to the fact that suppression of bone remodeling by bisphosphonates leads to an effete skeletal structure since bone remodeling (both the removal of old bone and new bone formation) is required to keep bone strength. As bisphosphonates are irreversible inhibitors, the removal of old bone in this carefully balanced system is suppressed, placing a patient at additional risk for a fracture.

Other biologics which directly treat osteoporosis and bone erosion include Denosumab, a fully human monoclonal antibody designed to block the effect of RANKL and possibly TNFα. However, higher incidences of infection have been reported in patients treated with Denosumab, possibly because of the off-target effect on TNFα. Another biologic is pulsed parathyroid hormone (PTH), a treatment which has been demonstrated to decrease bone fractures and increase bone density in postmenopausal osteoporosis. PTH targets osteoblasts to increase bone function and has shown great promise in the treatment of osteoporosis. However, the high cost of PTH (currently about $40,000 per year) has limited its use. Notably, neither PTH nor Denosumab have any noted effect of decreasing inflammation.

Osteoporosis is often associated with menopause (or any other loss of estrogen) in women and it has been established that osteoporosis is often associated with loss of estrogen. However, loss of estrogen also leads to other medical concerns. One of the more major of these is that loss of estrogen post-menopause also has been shown to lead to atherosclerosis (which is more commonly known as "coronary heart disease" or simply "heart disease") and certain cancers.

Atherosclerosis is the hardening and narrowing of the arteries which slowly blocks them and restricts blood flow. If arteries become sufficiently narrow, they can chock off blood flow to vital organs (often the heart or brain) which can cause heart attacks and strokes, two of the leading causes of death and major hospitalization in the United States. Atherosclerosis begins with a thin layer of cells called the endothelium. The endothelium keeps the inside of arteries toned and smooth, which keeps blood flowing. When the endothelium is damaged (e.g. it develops legions) LDL cholesterol will enter the wall of the artery. Endothelium damage can be caused by a wide variety of factors, but many of the more recognized are smoking, high blood pressure, and high cholesterol.

When LDL cholesterol enters the wall of the artery, white blood cells will also enter the wall to digest the LDL. Over years, cholesterol and cells become plaque in the wall of the artery. These plaques result in the hardening and narrowing of the artery. They can also rupture allowing blood in the bloodstream to clot, which creates additional issues as the clot can result in a sudden loss of blood flow and be characteristic of a heart attack or stroke.

Atherosclerosis is incredibly common. It has been estimated that at least 50% of people over the age of 40 have it with as many as 85% of those over 50 having at least some formed plaques. While it is a disease generally associated with aging, at least one study has shown that 17% of teenagers still have some formed plaques as well. Interestingly, pre-menopausal women are at a reduced risk of atherosclerosis as naturally occurring estrogen appears to assist in both LDL cholesterol regulation and assists in resisting damage to the endothelium. However, post-menopause, the loss of estrogen results in women having an increased risk.

Atherosclerosis is, in many respects, untreatable. Once a plaque has formed it will be with the patient for the rest of their life. Thus, treatments often focus on reducing or eliminating the formation of plaques and many treatments focus on prevention. In particular, many treatments focus on traditional healthy living activities focusing on regular exercise and improved diet earlier in life.

Once Atherosclerosis reaches a certain stage, it is usually necessary to supplement preventative therapies with those that focus on minimizing effect. Drug therapies, therefore, often focus on redaction of exaggerating factors to slow plaque formation or build up. Typically, therapeutic avenues include ameliorating dyslipidemia (with statins, PCSK9 inhibitors, fibrates, or other inhibitors of dietary cholesterol absorption); ameliorating hypertension (with diuretics, angiotensin receptor blockers, Ca-channel blockers, or beta-blockers); or with anti-thrombotic agents (aspirin, clopidogrel, or warfarin). Once plaques become to large, bypass surgery or the introduction of stents is generally required.

SUMMARY OF THE INVENTION

Because of these and other problems in the art, described herein, among other things is a method for inhibiting Atherosclerosis, the method comprising: providing a low-dose of RANKL to a patient; and generating in vivo the patient, FoxP3+ CD8 T-cells ($Tc_{REG}$); repeating said providing according to a repeating schedule so as to provide the RANKL at pulsed intervals. The pulsed interval administration then results in reduction in osteoporosis and a decrease in the number of atherosclerotic lesions in the aortic root.

Systems and methods for inhibiting bone loss using FoxP3+ CD8 T-cells ($Tc_{REG}$). Osteoclasts are induced to produce FoxP3+ CD8 T-cells ($Tc_{REG}$) through introduction of a low-dose of a RANK agonist such as RANKL. The RANKL was found to best work when provided in accordance with a schedule resulting in a pulsed administration.

There is also described herein a method for inhibiting atherosclerosis in a patient, the method comprising: providing said patient a RANK agonist being of: sufficient amount to induce osteoclasts of said patient to produce FoxP3+ CD8 T-cells ($Tc_{REG}$); and insufficient amount to activate enough of said osteoclasts to create bone loss in said patient; and repeating said providing according to a fixed schedule so as to provide said RANK agonist to said patient at pulsed intervals.

In an embodiment, the patient is a postmenopausal female.

In an embodiment of the method, the RANK agonist is RANKL.

In an embodiment of the method, said sufficient amount comprises 0.125 mg/kg RANKL or less. In other embodiments, said sufficient amount comprises 0.5 mg/kg or 0.05 mg/kg or less.

In an embodiment of the method, the pulsed intervals are about every 28 days.

BRIEF DESCRIPTION OF THE DRAWINGS

FIG. 1A shows the numbers of FoxP3+ CD8 T-cells ($Tc_{REG}$) that are found in the bone marrow and spleen are plotted (y-axis) as a function of RANKL dose (x-axis). FIG. 1B shows that to test for $Tc_{REG}$ induction by RANKL activated osteoclasts, congenically marked (Thy 1.2) GFP negative CD8 T-cells (see panel C for FACS plots) were adoptively transferred into Thy 1.1 OT-I Rag$^{-/-}$ mice. In the absence of RANKL treatment, very low level of conversion was observed after three days. Low dose (0.125 mg/kg) RANKL robustly induced $Tc_{REG}$; $Tc_{REG}$ induction was measured 50 hrs after RANKL treatment and 3 days after T-cell transfer. The induction required active osteoclasts as no induction of $Tc_{REG}$ was observed in mice pre-treated with Zoledronic acid (ZA). ZA was administered intravenously one week prior to adoptive transfer of CD8 T-cells. FIG. 1C shows representative FACS plots for FIG. 1B.

FIG. 2A shows that the abundance of $Tc_{REG}$ in sham-operated mice was similar to the levels found in ovariectomized (OVX) mice. FIG. 2B shows that $Tc_{REG}$ purified by magnetic beads from sham-operated, ovariectomized and WT mice treated with low-dose (0.125 mg/kg) RANKL were tested in a matrix dissolution assay. All $Tc_{REG}$ suppressed bone resorption by osteoclasts.

FIGS. 3A and 3B show that the pro-inflammatory cytokines IL-17A and TNFα suppress $Tc_{REG}$ induction by osteoclasts. FIG. 3A shows that $Tc_{REG}$ induction was tested using bone marrow cells-derived osteoclasts, pulsed with SIINFEKL ovalbumin peptide. $Tc_{REG}$ induction was observed in OT-I T-cells in the absence of (0 ng/ml) but significantly reduced in the presence of 10 ng/ml IL-17A. FIG. 3B shows that TNFα also reduced $Tc_{REG}$ induction in a dose dependent manner. To test if the ratio of TNFα to RANKL concentration affected suppression of $Tc_{REG}$ induction, the assay was performed with 50 or 100 ng/ml RANKL in the culture media. ANOVA analysis to determine the variation due to TNFα and RANKL concentration indicates that TNFα accounted for 85.5% of the total variance (P<0.0001) and RANKL accounted for 0.65% of the total variance (P<0.001). The interaction term accounted for remaining 9.3% of the total variance indicating that TNFα had a strong effect at each concentration of RANKL tested.

Figure 4A:
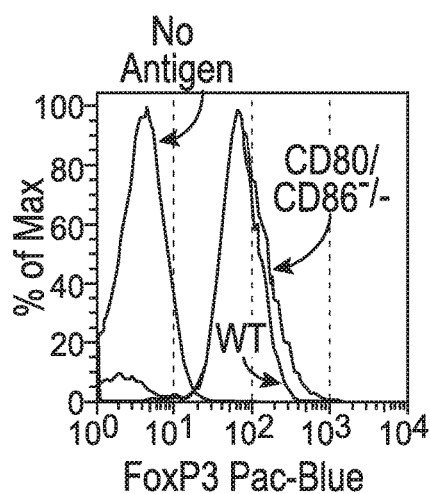
Figure 4B:
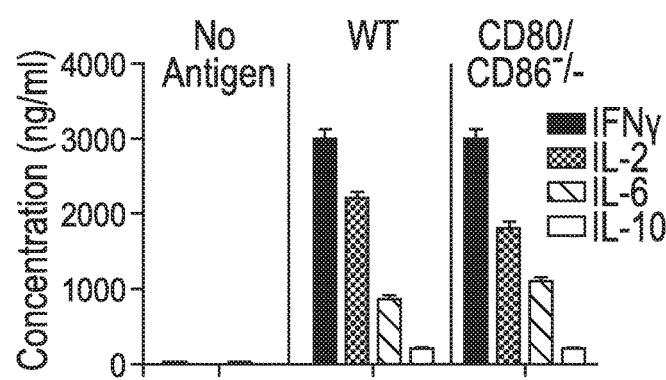
Figure 4C:
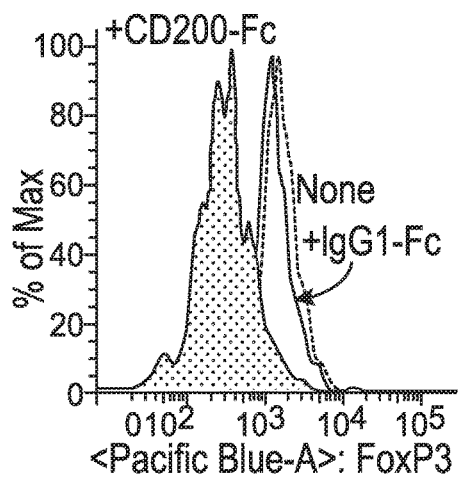
Figure 4D:
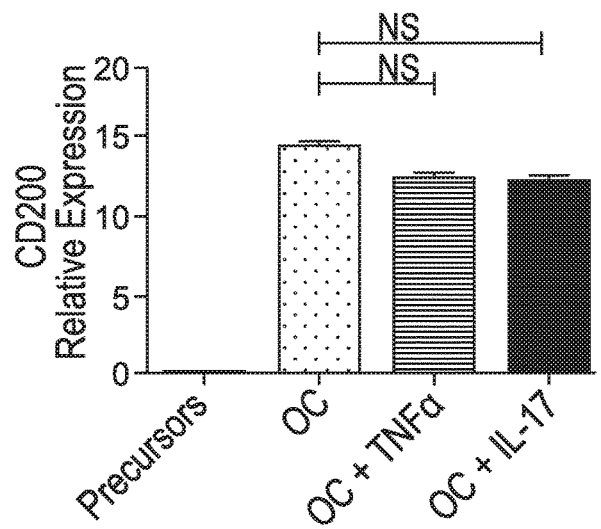

FIGS. 4A, 4B, 4C, and 4D show that CD200 but not CD80/CD86 are used by osteoclasts as costimulatory signal to T-cells. In FIG. 4A, Osteoclasts derived from bone marrow cells of CD80/CD86 doable knockout mice were capable of inducing $Tc_{REG}$ to a similar extent to wild-type (WT) derived osteoclasts. As shown in FIG. 4B, the levels of cytokines produced by $Tc_{REG}$ induced by WT osteoclast and CD80/CD86 double knockouts were indistinguishable. Taken together, these results indicate that CD80/CP86 are not used for costimulation of CD8 T-cells by osteoclasts. FIG. 4C shows soluble CD200-Fc added to OT-I CD8 T-cells prior to coculturing with osteoclasts blocked FoxP3 induction. FIG. 4D shows that CD200 expression is not detected in osteoclast precursors but is expressed in mature osteoclast. Recombinant murine TNFα (20 ng/ml) or IL-17A (10 ng/ml) had no effect on CD200 expression in mature osteoclasts.

Figure 5A:
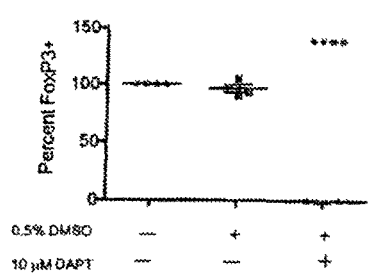
Figure 5B:
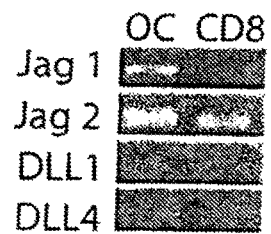
Figure 5C:
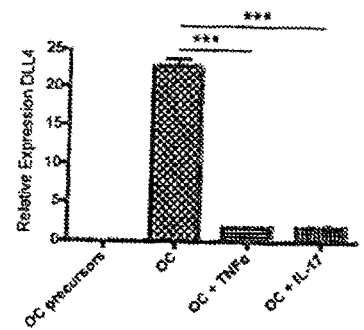
Figure 5D:
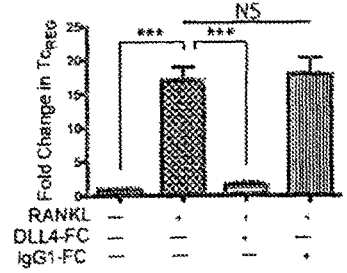
Figure 5E:
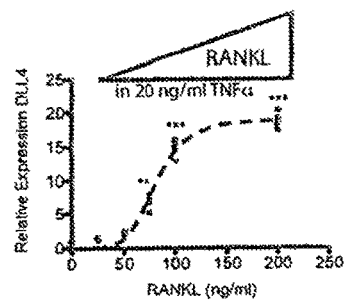
Figure 5F:
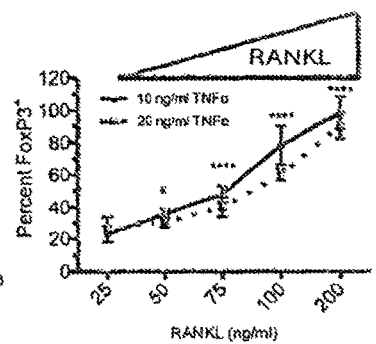

FIGS. 5A, 5B, 5C, 5D, 5E, and 5F show notch signaling by ligand DLL4, expressed on osteoclasts, induces $Tc_{REG}$. FIG. 5A shows that DAPT, a γ-secretase inhibitor, dissolved in DMSO was used to test the rote of Notch signaling in the induction of $Tc_{REG}$. 10 μM DAPT completely inhibited $Tc_{REG}$ induction. FIG. 5B shows that to determine which Notch ligands are expressed on osteoclasts and CD8 T-cells RT-PCR was used. Of the six Notch ligands encoded in the mouse genome, mature osteoclasts express Jagged (Jag)-1, Jag-2, Delta-like (DLL)-1 and DLL4. The CD8 T-cells also express Jag2 and DLL-1, FIG. 5C shows that of these four Notch ligands expressed in mature osteoclasts, only DLL4 was absent in the osteoclast precursors by qPCR. DLL4 expression was repressed in mature osteoclasts in the presence of recombinant murine 20 ng/ml TNFα and 10 ng/ml IL-17A. FIG. 5D shows that soluble DLL4-Fc, but not a control IgG1-Fc, administered 2 hours prior to RANKL administration blocked $Tc_{REG}$ induction in vivo. The experiment design of this in vivo induction experiment was identical to that used in FIG. 1B and 1C. FIG. 5E shows that addition of RANKL increased the expression of DLL4 even in the presence of 20 ng/ml RANKL. FIG. 5F shows that concomitant with the expression of DLL4, addition of RANKL also restores induction of $Tc_{REG}$ in the presence of 10 (solid line) or 20 ng/ml (dashed line) TNFα. ANOVA indicates that 90.7% of the variance was accounted for by RANKL treatment (P<0.0001), and 1.83% of the variance by TNFα treatment (P=0.0002). The interaction term accounted for 1.6% of the variance (P=0.0147) indicating that the effect of RANKL was dominant at both concentrations of TNFα tested.

Figure 6D:
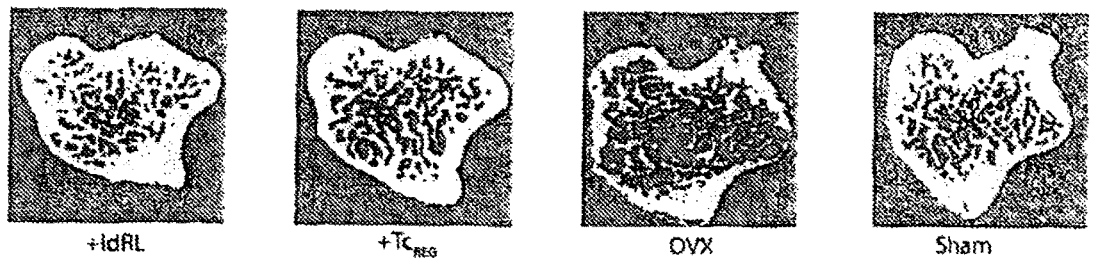
Figure 6E:
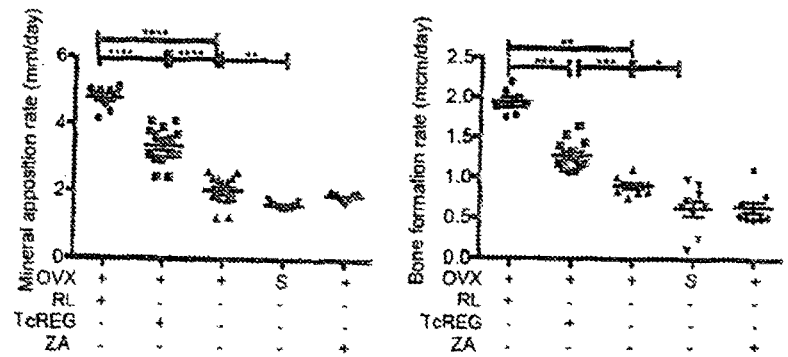
Figure 6F:
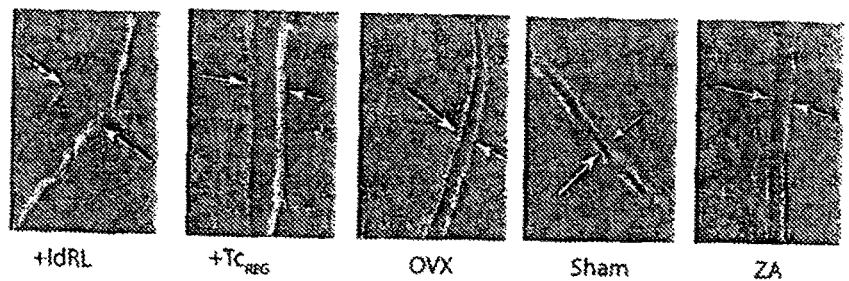

FIGS. 6A, 6B, 6C, 6D, 6E, and 6F show that Low dose RANKL induces functional $Tc_{REG}$ in ovariectomized mice. FIG. 6A shows that intraperitoneal administration of low dose RANKL (IdRL; 0.125 mg/kg) induced $Tc_{REG}$ in the bone marrow of ovariectomized mice. Representative FACS contour plots are shown on the first and second panel and the distribution (N=8 mice per group) is shown in the third panel. FIG. 6B shows that the serum CTX levels decreased in low-dose RANKL treated ovariectomized mice. In these experiments (panels C-F), we used ex vivo generated $Tc_{REG}$ as a positive control/comparator. FIG. 6C shows the femurs of low dose treated mice and control groups evaluated by μCT to determine ratio of bone volume to total volume (BV/TV; left panel) and bone mineral density (BMD; right panel). FIG. 6D shows representative images from distal femora. FIG. 6E shows that low dose RANKL treatment also increased mineral apposition rate (left panel) and bone formation rate (right panel) to a greater extent than Zoledronate and ex vivo generated $Tc_{REG}$. FIG. 6F shows representative images from the double-labeled femur (calcein green and alizarin red) from each group in FIG. 6E. Arrows are shown to emphasize the distance between dyes.

Figure 7A:
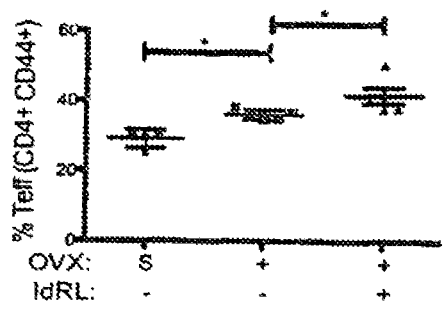
Figure 7B:
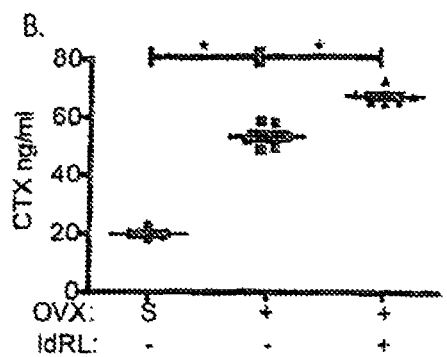

FIGS. 7A and 7B show the percent Teff (CD4+ CD4++) and CTX ng/ml.

Figure 8:
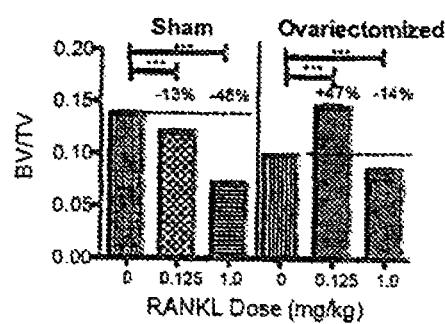

FIG. 8 shows the BV/TV for each RANKL Dose for Sham and Ovariectomized mice.

FIGS. 9A, 9B, 9C, 9D, 9E, and 9F provide various indications that dosing mice with RANKL provided for increased bone formation in mice.

FIGS. 10A, 10B, 10C, 10D, and 10E shows that pulsed dosing of RANKL provides for better results than continuous exposure and no exposure.

Figure 11A:
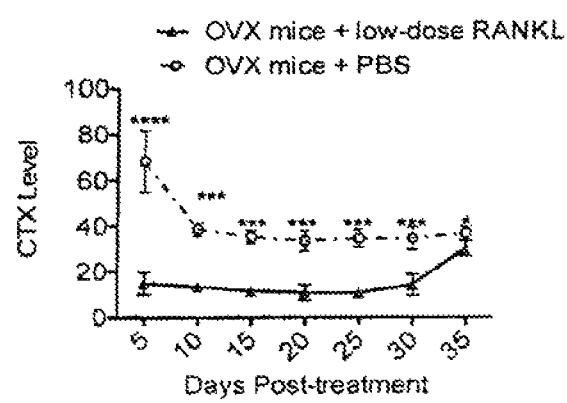
Figure 11B:
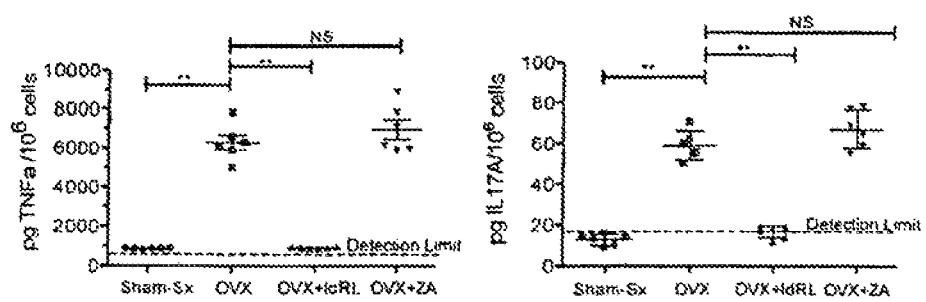

FIGS. 11A and 11B shows various indications of the value of a single treatment and multiple treatments.

Figure 12A:
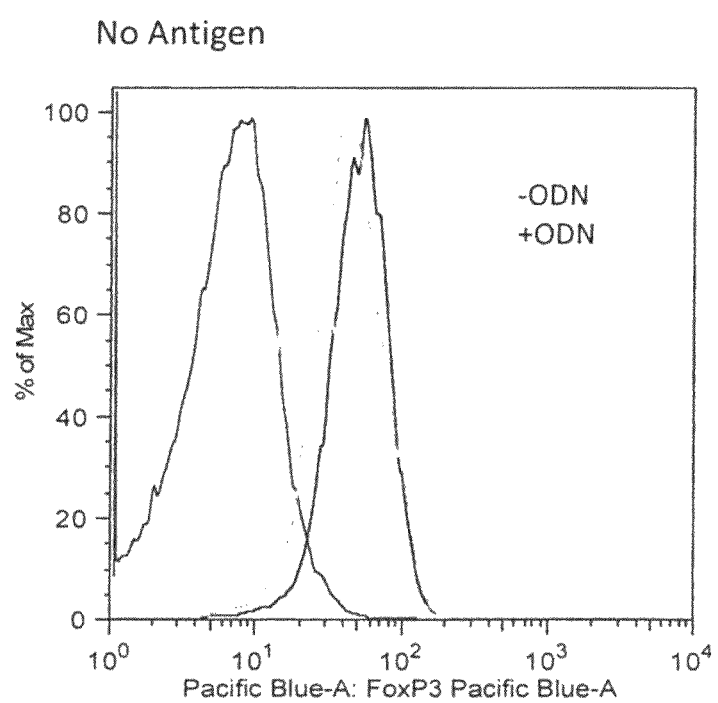
Figure 12B:
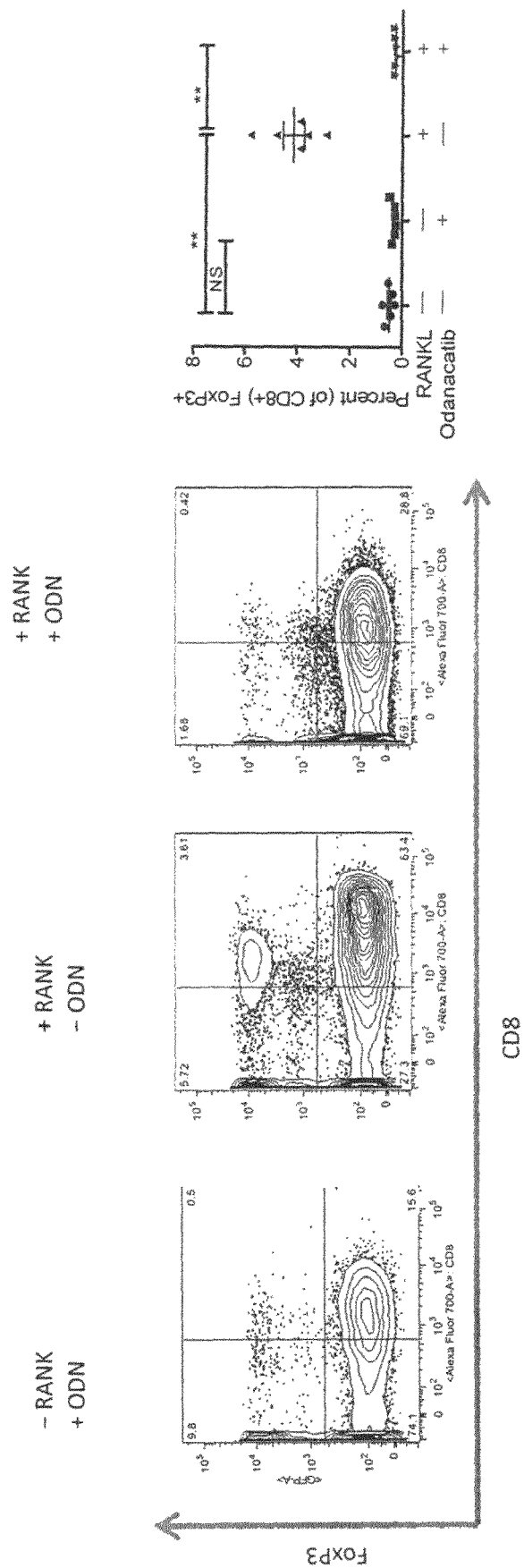

FIGS. 12A and 12B the effect of using Cathepsin K inhibitor is shown.

Figures 13A, 13B:
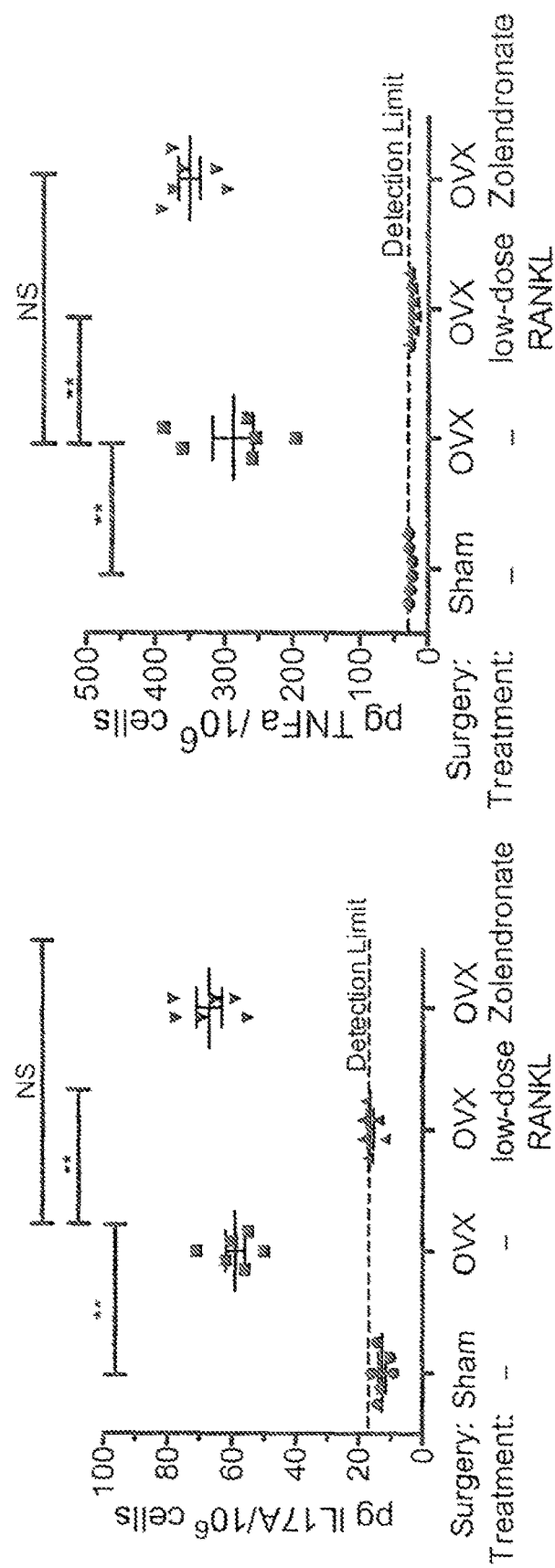

FIGS. 13A and 13B show that inflammation is increased upon ovariectomy in mice and the inflammation is decreased by low-dose RANKL treatment.

Figures 14A, 14B:
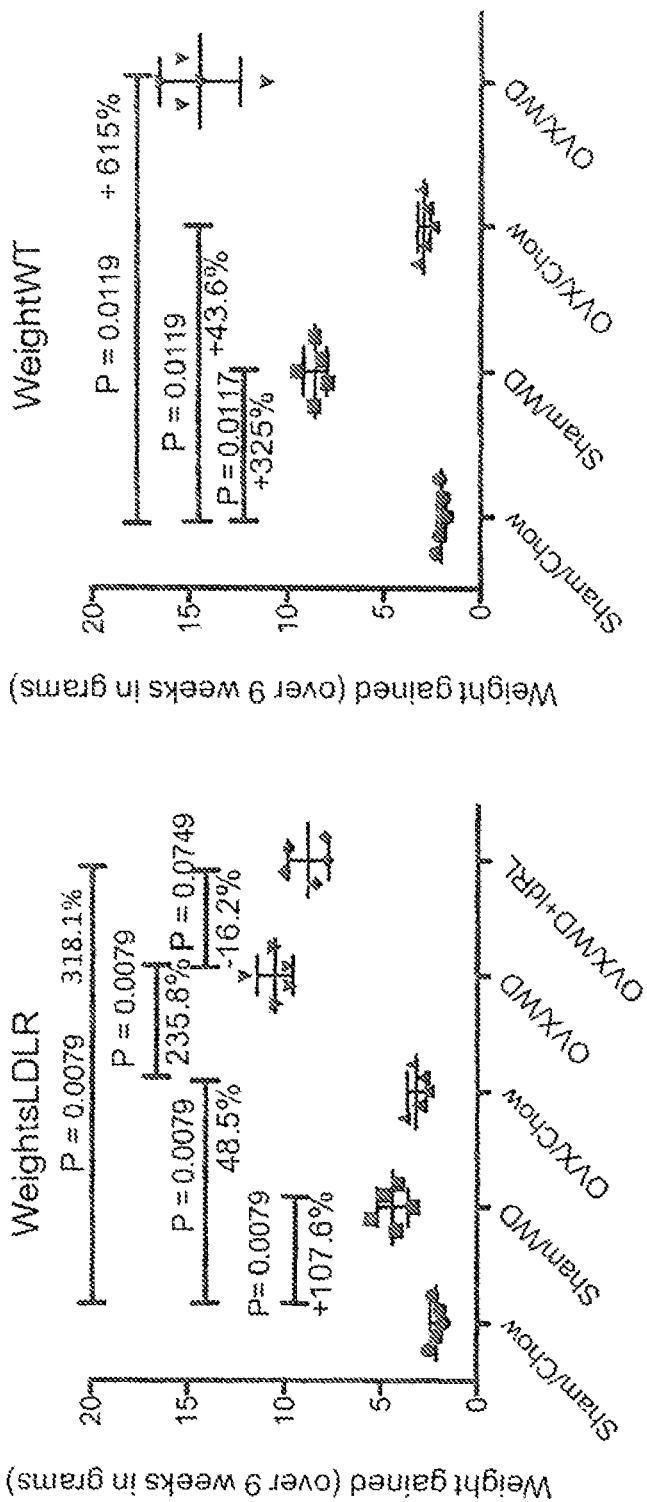

FIGS. 14A and 14B show the effect of ovariectomy and diet (chow vs. western diet) on weight, as well as the effect of including a low-dose RANKL treatment.

Figures 15A, 15B:
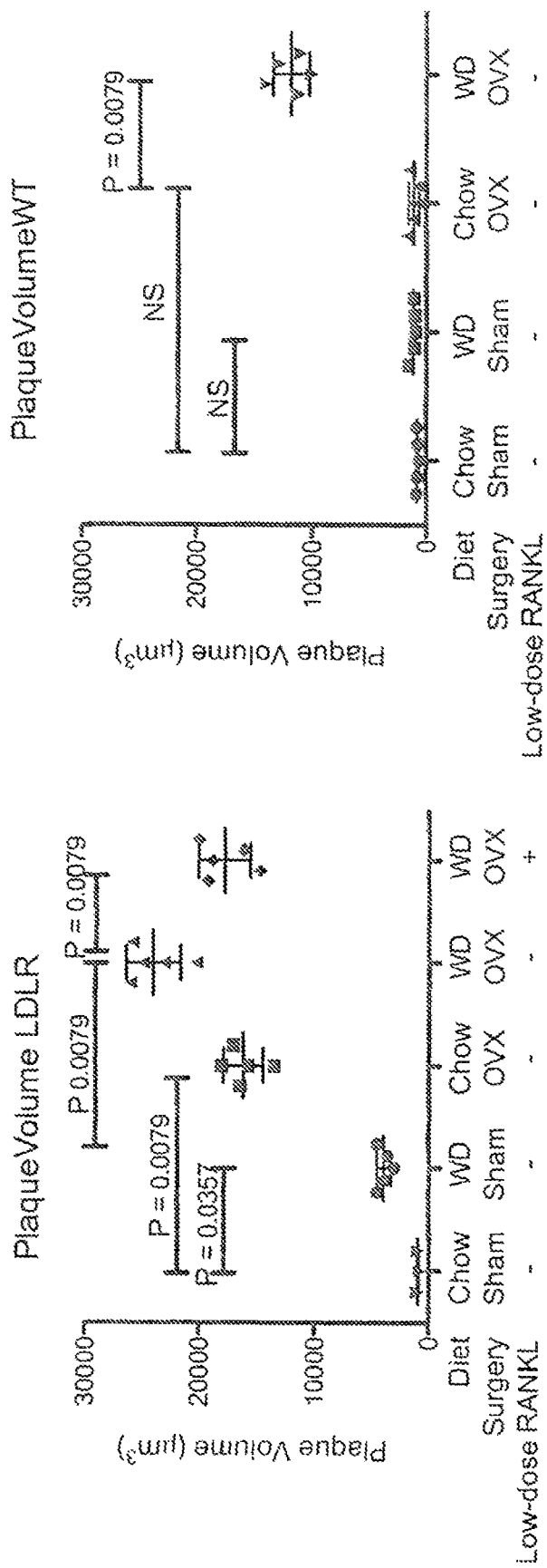

FIGS. 15A and 15B show the effect of ovariectomy and diet (chow vs. western diet) on atherogenesis (plaque formation), as well as the effect of including a low-dose RANKL treatment.

DETAILED DESCRIPTION OF PREFERRED EMBODIMENT(S)

It has been previously shown that osteoclasts recruit and activate CD8 T-cells and induce CD25 and FoxP3 expression in CD8+ T-cells. Further, both endogenous FoxP3+ CD8 T-cells ($Tc_{REG}$) and ex vivo generated osteoclast-induced regulatory T-cells (OC-i$Tc_{REG}$) suppress bone resorption in vivo. U.S. Pat. No. 9,144,599, the entire disclosure of which is herein incorporated by reference, provides for an ex vivo therapeutic method of generating $Tc_{REG}$.

The present disclosure provides for the induction of $Tc_{REG}$ in vivo. Active osteoclasts are generally needed to induce $Tc_{REG}$ in vivo. Yet, despite the increased activity and numbers of osteoclasts in ovariectomized mice, $Tc_{REG}$ levels remain unchanged. To understand the mechanism for the lack of $Tc_{REG}$ induction in ovariectomized mice, the signals provided by osteoclasts to induce $Tc_{REG}$ were investigated. Osteoclasts provide co-stimulation through CD200 and induced FoxP3 expression in CD8 T-cells through Notch ligand DLL4. The pro-inflammatory cytokines TNFα and IL-17 both suppressed the expression of DLL4 in mature osteoclasts, but this repression was reversed by addition of RANKL. To test for reversal of $Tc_{REG}$ induction by osteoclasts in vivo, low dose RANKL was administered to ovariectomized mice. As was the case in in vitro studies, RANKL induced functional $Tc_{REG}$ that suppressed bone loss. These results demonstrate that RANKL, while classically considered to promote bone resorption, at low doses leads to increased bone mass through activation of the osteoclast-$Tc_{REG}$ feedback loop. These results suggest that low dose RANKL may be used therapeutically to treat postmenopausal osteoporosis. The switching off of regulatory T-cell activation under inflammatory conditions may also be relevant for autoimmune diseases due to the failure of tolerance in endogenous regulatory T-cells.

Osteoimmunology is an emerging study of the crosstalk between the immune and skeletal systems. Osteoimmunology arose from the recognition that many cytokines produced by lymphocytes can affect bone homeostasis. While much is known about the cytokines and mechanisms that lead to bone erosion by the proinflammatory cytokines, much less is known about the mechanisms that maintain or restore homeostasis (i.e. the healthy state). One expects that there must be feedback loops in both the immune and skeletal systems that maintain and restore homeostasis after perturbations or changes to the system that arise due to abnormal (e.g. infections) and normal physiological processes (e.g. pregnancy).

Osteoclasts and CD8 T-cells form a novel negative feedback loop that contributes to the homeostasis of both the skeletal and immune system. We have previously shown that osteoclasts, cells of myeloid origin that resorb bone, recruit CD8 T-cells and crosspresent antigens (from exogenous proteins) to activate the CD8 T-cells. Osteoclast activated CD8 T-cell express CD25, FoxP3 and the following cytokines; receptor activator of NF-κB ligand (RANKL), interferon (IFN)-γ, interleukin (IL)-6, and IL-10. These osteoclast induced CD8 regulatory T-cells (in keeping with the recommendations for nomenclature, these cells are referred to as OC-iTc$_{REG}$ ) suppress bone resorption activity by suppressing actin ring reorganization in osteoclasts. Although they express RANKL which induces osteoclastogenesis, OC-iTc$_{REG}$ block osteoclast differentiation. Both the endogenous Tc$_{REG}$ and ex vivo generated OC-iTc$_{REG}$ suppressed bone resorption in mice in response to 1 mg/ml RANKL administration. Adoptively transferred OC-iTc$_{REG}$ also suppressed bone resorption by reducing the numbers of osteoclasts and reduced proinflammatory effector T-cells in ovariectomized mice. These results established that OC-iTc$_{REG}$ negatively regulate osteoclast activity and the immune system. Here we focus on the signals provided by osteoclasts to activate CD8 T-cells and induce FoxP3 expression.

Homeostasis, the ability to maintain a stable set point in response to physiologic of environmental changes, is achieved through a number of regulatory motifs. One of these motifs, referred to as the reactive negative regulation ensures that responses to stimuli are of the appropriate intensity, duration and are subsequently terminated or resolved. For example, acute inflammation is an appropriate and healthy response to an infection or trauma that clears or dilutes the offending agent and activates repair mechanisms. Acute inflammation is a healthy response as long as it is brief and intense enough to clear the infection and then resolves with minimal collateral damage. Pathologic situations may arise because the reactive regulatory systems fail to activate, leading for instance, to autoimmune disease, osteoporosis or chronic inflammation. Here, the ability of osteoclasts to induce Tc$_{REG}$ in vivo was evaluated. It was found that activation of osteoclasts is needed to induce Tc$_{REG}$, which is consistent with an expectation that Tc$_{REG}$ are reactive negative regulators. However, the question of what defect(s) in the osteoclast—Tc$_{REG}$ feedback system allows excess bone resorption in ovariectomized mice (and by inference in postmenopausal osteoporosis) remains unanswered.

Figure 1A:
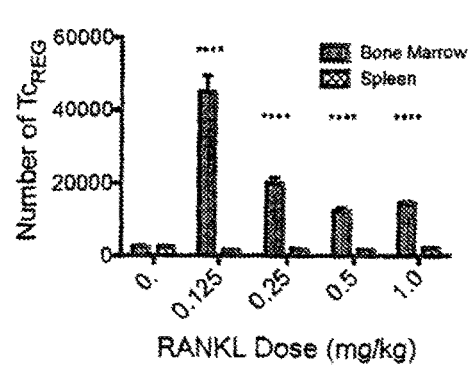
FIGS. 1A, 1B and 1C indicate that $Tc_{REG}$ are induced by activated osteoclasts.
Figure 1B:
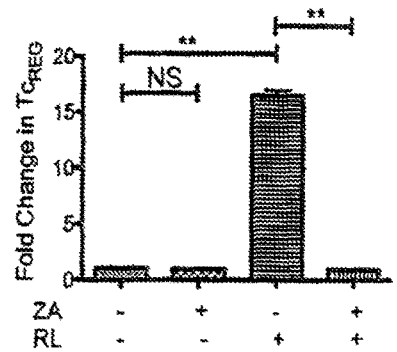
Figure 1C:
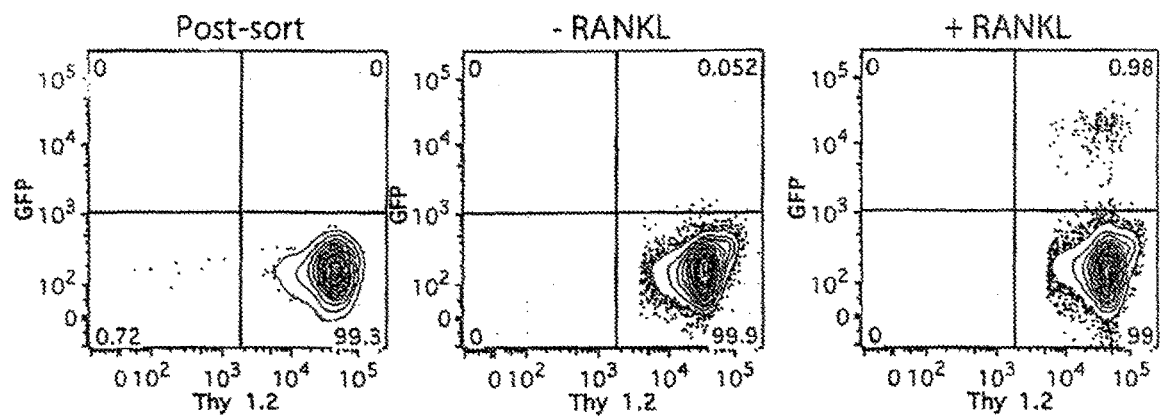

It was found that a low dose of RANKL activates osteoclasts to induce Tc$_{REG}$. It was first determined the dose of RANKL that produced the maximal number FoxP3$^+$ CD8 T-cells in the bone marrow. RANKL was administered into FoxP3-GFP reporter mice at various doses for two consecutive days. Fifty hours after first dose, the mice were sacrificed and the numbers of CD8 T-cells that were GFP positive cells in the bone marrow were measured. As shown in FIG. 1A, the lowest dose of RANKL (0.125 mg/kg) induced the largest proportion of FoxP3$^+$ CD8 T cells. The increased levels of FoxP3 in the bone marrow could either be due to recruitment of Tc$_{REG}$ to the bone marrow or induction of FoxP3 expression in cells that were FoxP3 negative. To test for induction we FACS sorted the GFP negative population of CD8 T-cells (Thy1.2$^+$ that were CD44 negative or naïve) from the spleens and bone marrow to high purity (FIG. 1C first panel) and adoptively transferred them into congenically marked (Thy 1.1) OT-I Rag$^{-/-}$ mice. The OT-I Rag$^{-/-}$ mice were used as recipients because they lack endogenous Tc$_{REG}$, which avoids competition and increases the sensitivity of the assay. In the absence of RANKL administration low levels GFP$^+$ CD8 T-cell were detected (FIGS. 1B and C second panel), but RANKL administration (0.125 mg/kg) yielded ≠1% GFP+ Thy1.2 T-cells (FIGS. 1B and 1C third panel). The conversion from GFP$^-$ to GFP$^+$ is a clear indication of induction of FoxP3 expression. To determine whether the activation of osteoclasts was needed for induction, we pretreated the OT-I Thy1.1 Rag$^{-/-}$ mice with the bisphosphonate, Zolendronic acid (ZA), one week prior to transferring GFP$^-$ cells. In mice treated with ZA, no conversion of CD8 T-cells to GFP$^+$ was observed indicating that actively resorbing osteoclasts are required for Tc$_{REG}$ induction.

Figure 2A:
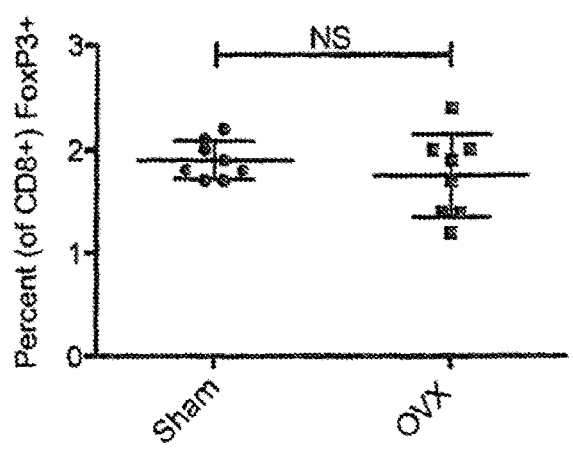
FIGS. 2A and 2B show that $Tc_{REG}$ levels are not affected by increased bone resorption in ovariectomized mice but the $Tc_{REG}$ can suppress osteoclast activity in vitro.
Figure 2B:
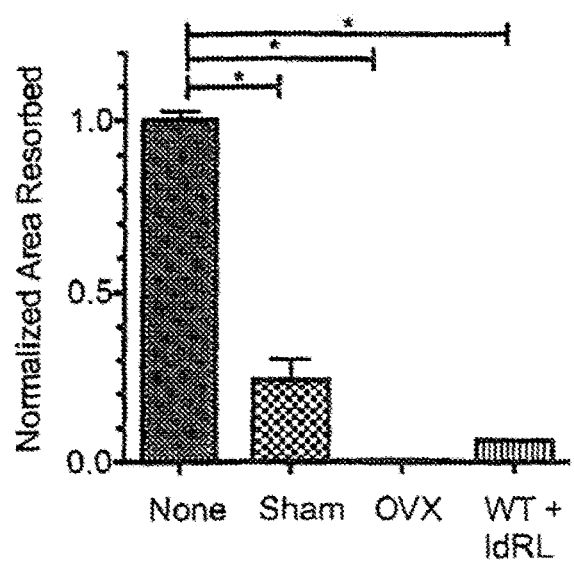

It was desired to verify that there are equivalent levels of Tc$_{REG}$ in ovariectomized and sham-operated mice. Previous findings indicate that both endogenous Tc$_{REG}$ and ex vivo generated OC-iTc$_{REG}$ suppressed bone resorption to maintain skeletal homeostasis. Tc$_{REG}$ therefore should be activated in ovariectomized, as estrogen depletion is known to activate osteoclasts. By this line of reasoning Tc$_{REG}$ should then suppress osteoclast activity. Therefore, as excess bone loss is observed in ovariectomized mice suggests that Tc$_{REG}$ are functionally lost. Therefore, we examined the levels of Tc$_{REG}$ in the bone marrow of sham operated and ovariectomized mice. As shown in FIG. 2A, Tc$_{REG}$ were present in ovariectomized mice, and there was no difference in the proportion of Tc$_{REG}$ found between the sham-operated and ovariectomized mice (24 days post-ovariectomy). At this time point, we also observed no significant difference between sham-operated and ovariectomized mice either in the overall number of cells or the proportion of CD8 T-cells in the bone marrow. We next considered the possibility that Tc$_{REG}$ are present but are non-functional. To assess the functionality of the endogenous Tc$_{REG}$, we isolated the GFP$^+$ CD8 T-cells from the bone marrow space of ovariectomized and sham operated mice by cell sorting. Equivalent numbers (5×10$^4$) of cells were tested using the bone matrix dissolution assay in vitro. As shown in FIG. 2, Tc$_{REG}$ from both the ovariectomized and sham operated mice effectively suppressed osteoclast bone resorbing activity. These results indicate that while the endogenous Tc$_{REG}$ are present and are functional in vitro, they are unable to limit bone loss in ovariectomized mice.

It was also determined that IL-17 and TNFα suppresses Tc$_{REG}$ induction by osteoclasts. One possible explanation for these results is that decreases in estrogen levels and/or the presence of pro-inflammatory signals cause osteoclasts in an ovariectomized mouse to be resistant to the suppression by Tc$_{REG}$. Another possibility is that loss of estrogen leads to increased production of the pro-inflammatory cytokines by T-cells that increase osteoclast activity. Without being limited to any method of operation, it is actually expected that in the presence of pro-inflammatory cytokines osteoclasts fail to induce $Tc_{REG}$. As estrogen depletion lead to greater number of osteoclasts because of a decreased Fas ligand expression, the loss of $Tc_{REG}$ induction and increased osteoclast numbers would tip the balance towards increased osteoclast resorption and net bone loss. To test for this possibility, OC-i$Tc_{REG}$ induction was measured in the presence of IL-17 and TNFα. Indeed, in the presence of 10 ng/ml IL-17 (FIG. 3A) or increasing TNFα concentration (FIG. 3B), the induction of $Tc_{REG}$ by osteoclasts was greatly impaired in a dose dependent manner. To understand the underlying mechanism of how TNFα affects osteoclasts' ability to induce $Tc_{REG}$, the signals provided by osteoclasts to induce FoxP3 in the CD8 T-cells were investigated along with if these signals were affected by TNFα or IL-17.

It was determined that Osteoclasts use CD200 as costimulatory signal to induce $Tc_{REG}$. Antigen presenting cells typically activate CD8 T-cells through three signals: antigen presented in the context of MHC class-I, a co-stimulatory signal, and finally a polarization signal that determines the effector phenotype of the T-cell. It has been previously shown that osteoclasts cross-present antigens, and antigen presentation is required for $Tc_{REG}$ induction. Here it was desired to identify the co-stimulatory signal provided by osteoclasts and to test if pro-inflammatory cytokines would regulate the expression of this molecule.

The most common and well-studied costimulatory signals on antigen-presenting cells are CD80 (B7.1) and CD86 (B7.2). As CD80/CD86 double knockout mice are commercially available, osteoclasts were generated from bone marrow precursors of these mice. The CD80/CD86 null osteoclasts (as well as wild-type controls) were then used to prime OT-I T-cells in the presence and absence of antigen. It was found that the osteoclasts derived from CD8G/CD86 null mice were able to induce $Tc_{REG}$ as effectively as wild-type controls (FIG. 4A). OT-I CD8 T-cells activated by CD80/CD86 null osteoclasts produced IL-6, IL-2 and IFN-γ to levels indistinguishable from wild-type mice (FIG. 4B). Having ruled out CD80/CD86 as the costimulatory molecules, an osteoclast microarray dataset was queried for other costimulatory molecules expressed by osteoclasts. Osteoclasts that express CD200 and c-Mer were found. The role of CD200 was chosen for testing based on the phenotype of CD200$^{-/-}$ mice and the reported role for CD200 in regulating $T_{REG}$. Treatment of OT-I CD8 T-cells with (soluble) CD200-Fc prior to co-culturing with osteoclasts impaired FoxP3 induction (FIG. 4C). In contrast, treatment of the OT-I CD8 T-cells with a control IgG1-Fc had no effect on FoxP3 induction. Consistent with a previous study, quantitative real-time PCR (qRT-PCR) shows that CD200 is not expressed in osteoclast precursors but is expressed in mature osteoclasts (i.e. was induced by RANKL in the precursors; FIG. 4D), CD200 mRNA expression levels are not altered by treatment of osteoclasts with TNFα or IL-17 (FIG. 4D).

It was also found that osteoclasts induce $Tc_{REG}$ using the Notch ligand DLL4. The most well characterized regulator of FoxP3 in T-cells is TGFβ. It has been previously shown that neutralization or addition of TGFβ has no effect on the induction of $Tc_{REG}$. Therefore identification of other pathways that can regulate the FoxP3 promoter in T-cells was sought. A number of previous studies have identified that the Notch signaling contributes to FoxP3 induction. To test if Notch signaling is important for $Tc_{REG}$ induction by osteoclasts, the γ-Secretase inhibitor DAPT was initially used. Ligation of the Notch receptor by its ligand leads to cleavage of Notch by γ-secretase. Inclusion of 10 μM DAPT in co-cultures of osteoclasts and OT-I CD8 T-cells completely abrogated FoxP3 induction (FIG. 5A). Next, we identified the Notch ligands expressed in osteoclasts using reverse-transcription followed by PCR. It was found that of the five Notch ligands encoded in the mouse genome, mature osteoclasts express: Jagged (Jag)1, Jag2, Delta-like (DLL)1 and DLL4 (FIG. 5B). Of the four, the osteoclast-precursors (bone marrow cells treated with M-CSF but not RANKL) express all of the ligands except DLL4 (FIG. 5C). To assess the role of DLL4 in $Tc_{REG}$ (soluble) DLL4-Fc was added to OT-I CD8 T-cells prior to co-culturing with osteoclasts. DLL4-Fc effectively abrogated $Tc_{REG}$ induction by osteoclasts (data not shown). To assess the role of DLL4 in vivo the induction experiments as described in FIG. 1 were performed: GFP negative (polyclonal) CD8 T-cells were purified by cell sorting and transferred into OT-II Rag$^{-/-}$ mice. Two hours prior in RANKL treatment, DLL4-Fc or a control IgG1-Fc, were injected intravenously into the recipient mice. As described for FIG. 1, RANKL (0.125 mg/kg) was then administered on two consecutive days. In mice receiving DLL4-Fc, no induction of $Tc_{REG}$ was observed (FIG. 5D). These results demonstrate that osteoclast use Notch ligand DLL4 to signal into CD8 T-cells to induce the expression of FoxP3.

DLL-4 expression is repressed in the presence of TNFα and IL-17 but can be de-repressed by RANKL. Having identified that DLL4 was required for osteoclasts to induce FoxP3expression in CD8$^+$ T cells we next tested if DLL-4 expression was affected by pro-inflammatory cytokines. As shown in FIG. 5C, DLL4 transcripts were significantly reduced in mature osteoclasts after culturing overnight in 20 ng/ml TNFα or 10 ng/ml IL-17. As RANKL induced DLL4 in osteoclast precursors, it was hypothesized that adding additional RANKL may overcome the repression of DLL4 by TNFα. To assess the reversibility of DLL-4 expression, mature osteoclasts were cultured overnight in 50 ng/ml RANKL and 20 ng/ml TNFα, and then additional RANKL was added to the culture media (while maintaining 20 ng/ml TNFα) as shown in FIG. 5E. Indeed, addition of RANKL overcomes (within 24 hours) the repression of DLL4 by TNFα as assessed by qRT-PCR. Based on this result, we tested the ability of RANKL to restore induction of $Tc_{REG}$ by osteoclasts. The experiment was performed as above, but in this case FoxP3 induction in OT-I CD8 T-cells in the presence of OVA and either 10 ng/ml or 20 ng/ml TNFα was measured. Consistent with restored expression of DLL4 on osteoclasts by RANKL the induction of $Tc_{REG}$ was also restored in the presence of TNFα. Our results indicate that TNFα repressed DLL4 expression and that addition of RANKL could de-repress the effect of TNFα leading to increased DLL-4 expression and to increased $Tc_{REG}$ induction by osteoclasts.

It was then determined that RANKL induces functional $Tc_{REG}$ in ovariectomized mice. Having shown that RANKL could restore the ability of osteoclasts to induce FoxP3 expression in the presence of TNFα in vitro, we tested the ability of RANKL to induce $Tc_{REG}$ in ovariectomized mice as proof of principle for de-repression by increased levels of RANKL in pro-inflammatory environment. Again, a dose of RANKL that induced the highest levels of $Tc_{REG}$ in vivo (FIG. 1A) was used. Administration of low dose RANKL to ovariectomized mice increased $Tc_{REG}$ numbers by an average of 1.8-fold (FIG. 6A). To determine whether this increase in $Tc_{REG}$ numbers affected bone resorption in ovariectomized mice, levels of bone resorption and bone formation rates in these (low-dose) RANKL-treated mice were measured. As it has been previously established that ex vivo generated OC-iTc$_{REG}$ limit bone resorption, increased bone mass, decreased activated effector T-cells, and increases bone formation and mineral apposition rates, this treatment was used as a benchmark in these experiments.

Ovariectomized mice treated with low dose RANKL had lower levels of serum CTX compared to mice treated with OC-iTc$_{REG}$ (FIG. 6B). The low dose RANKL-treated mice had fewer osteoclasts occupying bone indicating that low dose RANKL suppressed bone resorption and blocked osteoclastogenesis more effectively (FIG. 8). Accordingly, the low dose RANKL treated mice also had more bone mass and bone mineral density relative to the OC-iTc$_{REG}$ treated mice (FIG. 6C, 6D and FIG. 7). Finally, the low dose RANKL treated mice also had increase bone formation and mineral apposition rates than OC-iTc$_{REG}$ treated mice (FIG. 6E and F). These results indicate that low dose RANKL was a more effective treatment than OC-iTc$_{REG}$ and the bisphosphonate Zoledronic acid by all measurable criteria.

All organisms need to maintain physiological stability to survive changes in their environment. A number of mechanisms have evolved to achieve this physiological stability, chiefly positive and negative feedback loops. Our studies have revealed such a negative feedback loop between osteoclasts and CD8 T-cells that appears to be important for bone and immune homeostasis.

A low dose of RANK L generated the highest proportion of Tc$_{REG}$ in bone marrow (FIG. 1A). Further, RANKL-activated osteoclasts induce Tc$_{REG}$ (FIG. 1B). If active osteoclasts induce Tc$_{REG}$, which act as brakes on osteoclast activity to limit bone loss, why does menopause or ovariectomy lead to osteoporosis? As contemplated herein, despite the increased numbers and activity of osteoclasts in ovariectomized mice, no increase in the induction of Tc$_{REG}$ was observed (FIG. 2). The Tc$_{REG}$ present in ovariectomized mice were active, in that they were able to suppress bone resorption by osteoclasts in an in vitro assay. This result indicates that decrease in estrogen levels does not appear to mediate its effect on the activity of endogenous Tc$_{REG}$ (FIG. 2). Furthermore, transfer of ex vivo generated OC-iTc$_{REG}$ suppressed bone resorption indicating that decrease in estrogen levels does not render the osteoclasts incapable of responding to the suppressive mediators produced by Tc$_{REG}$. These results suggested osteoclasts were unable to induce Tc$_{REG}$ in ovariectomized mice (and perhaps in other inflammatory bone erosion diseases). To understand the-mechanism for the lack of Tc$_{REG}$ induction, Tc$_{REG}$ induction by osteoclasts in the presence of TNFα and IL-17 was examined. IL-17 was used because it has been previously shown that helper T-cells that express this cytokine (T$_H$17) increase bone loss. Inhibition of IL-17 signaling has also been shown to ameliorate bone loss in ovariectomized mice. Similarly, TNFα was used because levels of this cytokine increase in ovariectomized mice and disruption of TNFα signaling protects against bone loss post-ovariectomy. Consistent with lack of increase in ovariectomized mice, Tc$_{REG}$ induction was inhibited in the presence of TNFα or IL-17 in culture (FIG. 3).

To understand the mechanism for the loss of Tc$_{REG}$ induction, signals that osteoclasts provide to CD8 T-cells were examined. It has been previously demonstrated that antigen presentation is required for Tc$_{REG}$ induction. Here CD200 was identified as a costimulatory molecule used by osteoclasts to induce Tc$_{REG}$ (FIG. 4). While CD200 is induced by RANKL, the expression levels of CD200 were not affected by the presence of TNFα (20 ng/ml) or IL-17 (10 ng/ml; FIG. 4). Notch signaling has been previously been identified in affecting FoxP3 expression in T-cells[28,29,38]. Therefore, testing for the role of Notch signaling in Tc$_{REG}$ induction (FIG. 5A) was performed. Although osteoclasts express four Notch ligands (FIG. 5B), DLL4 was identified as expressed on osteoclasts that was required for FoxP3 expression in CD8 T-cells. DLL4 is only expressed in mature osteoclasts and not in osteoclast precursors suggesting that it is induced by RANKL (FIG. 5C). Administration of DLL4-Fc, but not a control IgG1-Fc, blocked induction of Tc$_{REG}$ in vivo (FIG. 5D). Furthermore, the expression levels of DLL4 were repressed in the presence of IL-17 and TNFα but that the repression was reversible by addition of RANKL (FIG. 5E). Indeed, concomitant with increased DLL4 expression by addition of RANKL, Tc$_{REG}$ induction by osteoclasts was restored (FIG. 5F).

Based on the in culture data, it was tested if low dose of RANKL could induce Tc$_{REG}$ in ovariectomized mice. Indeed, low dose RANKL administration robustly induced Tc$_{REG}$ in ovariectomized mice (FIG. 6A). The induced Tc$_{REG}$ were functional, in that they could suppress bone resorption as measured by serum CTX (FIG. 6B). The low-dose RANKL treated mice had increased bone mass (FIGS. 6C and D) and the bone formation and mineral apposition rates were markedly increased (FIGS. 6E and F). The in vivo induced Tc$_{REG}$ were more effective at ameliorating osteoporosis than adoptively transferred OC-iTc$_{REG}$, possibly because their local concentration is higher as they are induced by osteoclasts at the bone-remodeling site by RANKL. It is remarkable that administering low dose RANKL leads to reduced bone loss and increased bone formation because RANKL is exclusively believed to be a pro-resorptive. This result could not be predicted or understood in the absence of the knowledge of the osteoclast-Tc$_{REG}$ feedback loop. Furthermore, studies provide a mechanism of why the endogenous Tc$_{REG}$ are not induced to suppress excess bone loss: pro-inflammatory cytokines like TNFα and IL-17 suppress the expression of DLL4, which is needed for FoxP3 induction in CD8 T-cells by osteoclasts. Unexpectedly, DLL4 acts as a simple switch for Tc$_{REG}$ induction in response to TNFα and RANKL. At doses above 0.5 mg/kg RANKL and prolonged (>5 days) dosing promotes bone resorption in estrogen-replete and estrogen-depleted mice.

Since RANKL promotes bone resorption anti-RANKL therapies, like Denosumab, have been used to suppress bone loss. Indeed, the efficacy of anti-RANKL therapy has been demonstrated in clinical trials for Denosumab. Therefore, one explanation of these results is that RANKL has biphasic response; whereas at low doses it is beneficial, at high doses RANKL is toxic, in that it leads to excess bone loss. There are a number of demonstrated examples in biology of mediators that produce a biphasic response. Yet curiously, if the levels of RANKL are high such that Denosumab is effective, how can such a low dose of RANKL effectively activate osteoclasts to induce Tc$_{REG}$? We conjecture that it is not the absolute concentration that is important but instead a pulse of RANKL that activates osteoclasts to produce Tc$_{REG}$. The in vitro data that RANKL induces DLL4, regardless of TNFα concentration. (FIGS. 3B and 5F) is consistent with this view. Since it is technically difficult to accurately measure the concentration of (soluble and bound) biologically available RANKL (produced by osteoblasts, osteocytes, T-cells and other cells) in the bone marrow, experimentally verifying this conjecture is outside the scope of this work. It is also noted in this regard that parathyroid hormone (PTH) demonstrates a similar behavior: whereas, intermittent doses of PTH are anabolic, continuous exposure lead to bone loss[44].

Regulatory T-cells ($T_{REG}$) are a subset of $CD4^+$ T cells that play a critical role in negatively regulating self-reactive T-cells and in resolving inflammatory responses. It is well documented that a reduction in the number and/or function of $T_{REG}$ causes the breakdown of immunologic self-tolerance leading to autoimmune diseases. However, it is not clear why $T_{REG}$ fail to control inflammation in individuals with autoimmune diseases. One reason suggested for this loss of tolerance is due to $T_{REG}$ instability (or more explicitly conversion of $exT_{REG}$ to $T_H17$ cells) when exposed to an inflammatory environment. The present inquiry into why $Tc_{REG}$ fail to suppress osteoclast activity and allow osteoporosis to develop followed a similar line of investigation. Results indicate that inflammatory cytokines (FIG. 3) do not lead to defects in $Tc_{REG}$, but suppress induction of $Tc_{REG}$ by osteoclasts (i.e. the antigen-presenting cells) through regulating DLL4 expression (FIG. 5). By extension, the results are consistent with the emerging paradigm that inflammatory cytokines (i.e. induced by adjuvant or PAMPS) affect the antigen-presenting cells, and not the $Tc_{REG}$, to tip the balance from induction of tolerance towards immunity.

As shown above, low doses of RANKL activate osteoclasts to induce $Tc_{REG}$. Further, in the presence of TNFα and IL-17, $Tc_{REG}$ induction is suppressed. CD200 and DLL4 were identified as costimulatory and differentiation signals respectively, used by osteoclasts to induce $Tc_{REG}$. Furthermore, TNFα and IL-17 were demonstrated to suppress DLL4 expression, and thus providing a plausible mechanism for why despite increased activity of the osteoclasts in ovariectomized mice, $Tc_{REG}$ levels are not increased. Thus, in vitro DLL4 acts as a simple switch that responds to TNFα and IL-17 to turn off $Tc_{REG}$ induction. RANKL turns on DLL4 expression and concomitantly $Tc_{REG}$ induction. Finally, low dose RANKL induces functional $Tc_{REG}$ in ovariectomized mice leading to lower bone resorption, increased bone mass and density, and increased formation of new bone. Thus, a low dose RANKL pulse has the potential to be a new therapy to treat postmenopausal osteoporosis and perhaps other inflammatory bone erosion diseases. Low dose RANKL therapy offers an advantage over anti-RANKL, bisphosphonate and intermittent PTH therapy because it not only inhibits bone resorption and promotes new bone formation, but because as we have previously shown, $Tc_{REG}$ also decrease the levels of pro-inflammatory effector T-cells in ovariectomized mice[10] and have the potential to restore immune homeostasis as well. This is discussed in greater detail later in this disclosure, In order to obtain the above discussed results, C57BL/6 mice were purchased from Jackson Labs or used from in-house breeding colonies. Breeders of $FoxP3^{eGFP}$ reporter (model 006769) mice on a C57BL/6 background were purchased from Jackson Labs, and bred in-house for these experiments. OT-I $Rag^{-/-}$ mice were purchased from Taconic. Breeders of OT-I Thy1.1 $Rag^{-/-}$ mice were a gift of Dr. Ryan Teague (St. Louis University School of Medicine). All animals were maintained in the Department of Comparative Medicine, Saint Louis University School of Medicine in accordance with institutional and Public Health Service Guidelines.

Bilateral ovariectomy was performed on 12-14 week old mice. Mice were anesthetized using 2.5% isoflurane to initiate anesthesia, and 1% for maintenance. The ovaries were accessed through a single incision in the skin, and exteriorized through muscle wall on each side. Each ovary was clamped using hemostat and removed by a single cut. Skin staples (3M) were used to close the skin incision. To minimize discomfort post-surgery, 0.025 mg/kg Buprenorphine was administered subcutaneously. Zoledronate (Selleck Chemicals) was administered at 30 µg/kg via tail vein.

All T-cells were transferred via tail vein. For injections mice were restrained and $20 \times 10^6$ T-cells, suspended in 100-150 µl PBS were injected into the lateral vein.

OC precursors were isolated as previously described. Briefly, the mice were sacrificed by CO2 asphyxiation and the long bones harvested. One end cap of the bone was removed and the long bones were placed in a 0.7 ml microcentrifuge tube, pierced with a 22 G needle at the bottom of the tube. The 0.7 ml tube was fitted inside a 1.5 ml microcentrifuge tube. The assembly was spun for 30 seconds at 16,000×g. The bone marrow cells were resuspended in α-minimum essential medium (αMEM, Invitrogen), and filtered through a 40 µ cell strainer. The cells were pelleted, resuspended and maintained in αMEM growth medium (αMEM supplemented with 10% heat-inactivated fetal bovine serum [Invitrogen]), penicillin-streptomycin-glutamine (Invitrogen) and recombinant murine M-CSF (Peprotech) at 20 ng/ml). OC were generated by addition of recombinant murine GST-RANKL to a final concentration of 50 ng/ml. M-CSF and GST-RANKL were added every 48 to 72 hours.

Single cell suspensions of spleens were prepared in PBS+ 1% FBS by grinding with a sterile syringe plunger and dispersed by pipetting, then filtering through a 40 µ cell strainer. For co-culture experiments, OT-II CD4 or OT-I CD8 T-cells were prepared by first enriching for T-cells using Pan-T-cell beads then purified by negative selection using appropriate magnetic beads (Miltenyi). All bone marrow and splenic T-cells purified by positive selection were incubated for 30 m at 37° C. to allow cells to allow dissociation or uptake of bound beads from cell surface. The resulting T-cells were routinely>97% pure when stained with anti-CD3, anti-CD4 and anti-CD8 antibody.

Day 4 OC cultured in 20 ng/ml M-CSF and 50 ng/ml GST-RANKL, were seeded at $5 \times 10^5$ cells/well in the presence of 5 µM OVA (A-5503; Sigma-Aldrich) in 24-well tissue culture-treated plates (Corning). After 14-16 hours of incubation, medium was removed and (adherent) cells were washed with pre-warmed medium. $2.5 \times 10^5$ freshly harvested splenic OT-I transgenic T cells purified by negative selection were added in 2 ml of complete T-cell media (RPMI, 10% ΔFBS, penicillin-streptomycin-glutamine, non-essential amino acids, sodium pyruvate, HEPES, and 55 µM β-mercaptoethanol). Following 48 hours co-culture, T-cell aliquots were removed and stained intracellularly to assess FoxP3 expression. The $Tc_{REG}$ were then further expanded, in the absence of OC, by splitting cells 1:2 and culturing in 100 U/ml IL-2 containing T-cell media for an additional 48 hours. For polyclonal $Tc_{REG}$ generation, T-cells were purified from spleens of C57BL/6 mice and incubated with day 4 OC in the presence of 1 µg/ml anti-CD3. Control T-cells were activated with plate bound anti-CD3 (1 µg/ml) and anti-CD28 (2 µg/ml; both from eBiosciences) for 48 hours; the activated T-cells were expanded further by splitting 1:2 and culturing for additional 48 hours in IL-2 (100 U/ml). $20 \times 10^6$ $Tc_{REG}$ (in 200 µL) were then injected by tail vein into 8-week-old OT-I mice.

Osteoclasts seeded on day 4 at $1.5 \times 10^6$ cells/ml were used in all experiments. RNA was isolated at time point described in Figure legends. 10 to 50 ng of RNA was used for first-strand cDNA synthesis in 50 µL reaction per kit instructions (Superscript III cDNA synthesis system; Invitrogen).

In all cases ≠10% of the cDNA product was used in a 50 μL PCR reaction that contained 10 μM each forward and reverse primers. For quantitative PCR (qPCR) SYBR green system (Invitrogen) was used. Otherwise, cDNA was amplified (25 cycles) and the products resolved on 1.2 % agarose gel and visualized by ethidium bromide staining.

Anti-mouse antibodies for Fluorescence Activated Cells Sorting (FACS) were: PE-conjugated anti-mouse CD8a (clone 53-6.7; BD Pharmingen), AF700-conjugated anti-mouse CD44 (IM7; BD Pharmingen), e450-conjugated anti-mouse FoxP3 (FJK-16s, eBioscience), anti-CD3e (500A2; Biolegend), anti-CD8a (5H10; Caltag), anti-CD4 (RM4-5; BD Pharmingen), V450-conjugated CD45.1 (A20; BD Biosciences), PE-Cy7 conjugated anti-CD45.2 (104; BD Biosciences) and anti-CD25 (Clone PC61; BD Pharmingen). Functional grade anti-CD3 (17A2) and anti-CD28 (37.51) were purchased from eBioscience. For FACS cells were blocked with anti-mouse FcgRIII/IIR (BD Pharmingen) for 10 m and then stained for 45 m on ice with fluorophore-conjugated antibody. Stained cells were washed, fixed with 3% paraformaldehyde and analyzed on LSRII instrument with CellQuest (BD Biosciences) software. Data analyses were performed with FlowJo software (version 8.73; Tree Star).

Food was withdrawn 6 to 10 hours prior to bleeding. Peripheral blood (100 to 200 μL) obtained via sub-mandibular vein, was allowed to clot for 2 hours at room temperature and serum collected by spinning down the cell pellet. Serum C-terminal telopeptide of type 1 collagen (serum CTX) was measured using ELISA according to the manufacturer's instructions (Immunodiagnostic Systems, Plc.)

CD8 T-cells were isolated from the bone marrow cells (isolated as described in OC generation section above) using magnetic beads. The $Tc_{REG}$ were further purified in some experiments by cell sorting and co-cultured with OC ($5\times10^5$) that were previously seeded on 24-well hydroxyapatite coated plates (Corning). M-CSF and GST-RANKL were added every 48 hours. On day 5, cells were removed with 10% bleach and pit area was photographed and quantified using NIH ImageJ.

The bones were scanned in μCT40 (Scanco Medical) at 55 kVp, 145 μA, and resolution of 16 μm. Gauss sigma of 1.2, Gauss support of 2, lower threshold of 237, and upper threshold of 1000 were used for all the analysis. Regions of interest were selected 50 slices below the growth plate of the proximal tibia to evaluate the trabecular compartment. Bone mineral density was obtained by quantitative μCT using Scanco Phantoms for calibration[49]. All μCT data and bone histomorphometry data was collected and analyzed by C.Y. who was blinded to the treatment performed on the mouse samples.

Statistical significance was assessed in all cases using paired two-tailed Mann-Whitney U test in GraphPad Prism 5.0 f. One-way and two-way ANOVA was performed in GraphPad Prism 5.0 f.

As contemplated above, pulsing ovariectomized mice with low-dose RANKL, suppressed bone resorption, decreased the levels of proinflammatory effector T-cells and had a bone anabolic effect. This effect of RANKL is mediated through the induction of regulatory CD8 T-cells by osteoclasts. Thus it was expected that pulses of low-dose RANKL would be needed to induce $Tc_{REG}$ and this was verified as continuous infusion of identical dose RANKL by pump did not induce $Tc_{REG}$. It was determined that low-dose RANKL can induce $Tc_{REG}$ at two, three, six and eight-weeks post-ovariectomy. Results show that low-dose RANKL treatment in ovariectomized mice is optimal at once per month to maintain the bone mass. It was also found that treatment of ovariectomized mice with the Cathepsin K inhibitor, Odanacatib (ODN), also blocked $Tc_{REG}$ induction by low-dose RANKL. Without being bound by any method of operation, this is interpreted to indicate that antigens presented to CD8 T-cells by osteoclasts are derived from the bone protein matrix because ODN inhibits Cathepsin K, which mediates the breakdown of collagen and other proteins present in the bone. It is thus believed that basis low-dose RANKL (or a RANK agonist), particularly via a pulsed delivery systems, provides a therapeutic for postmenopausal osteoporosis or any other form of bone loss.

Figure 9A:
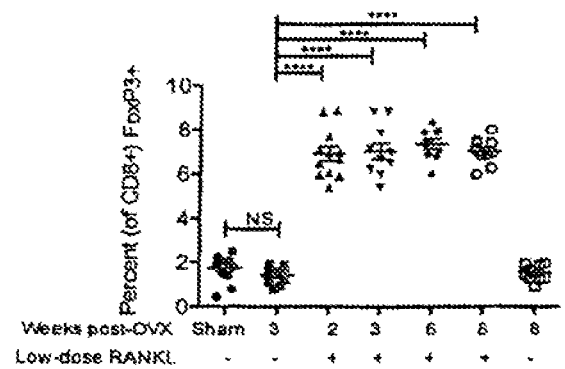
Figure 9B:
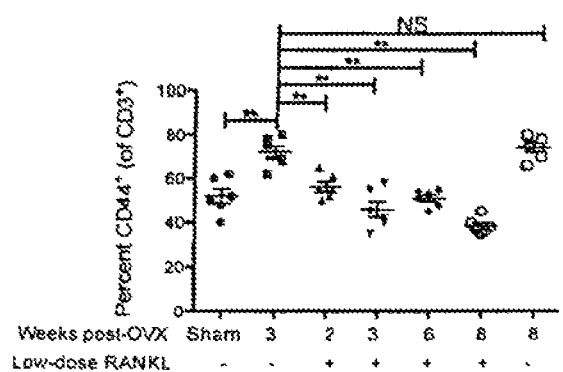
Figure 9C:
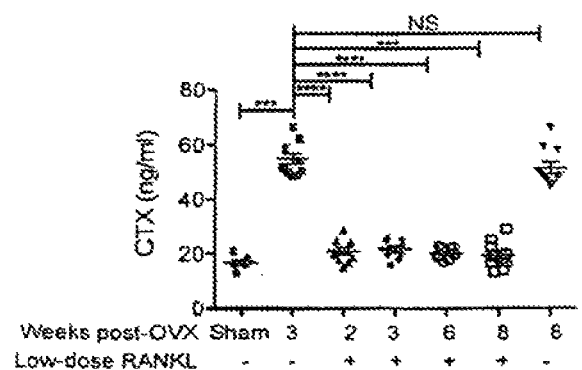
Figure 9D:
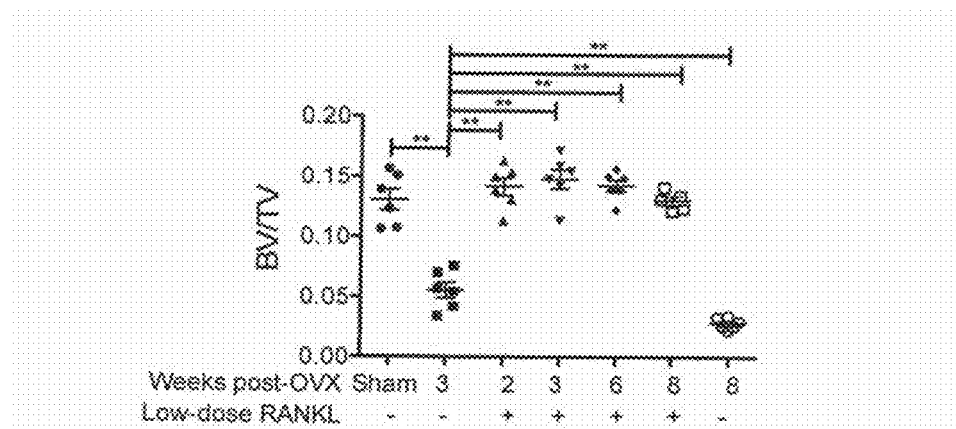
Figure 9E:
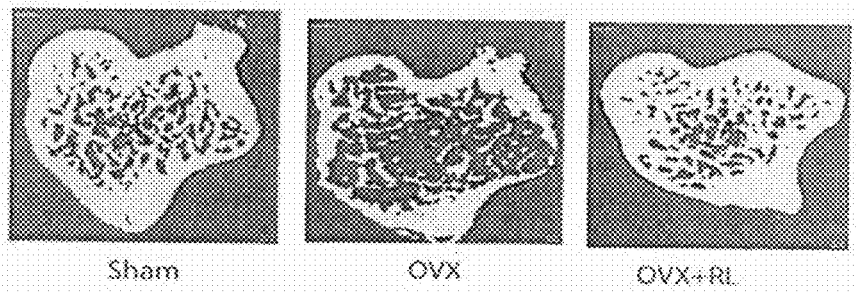
Figure 9F:
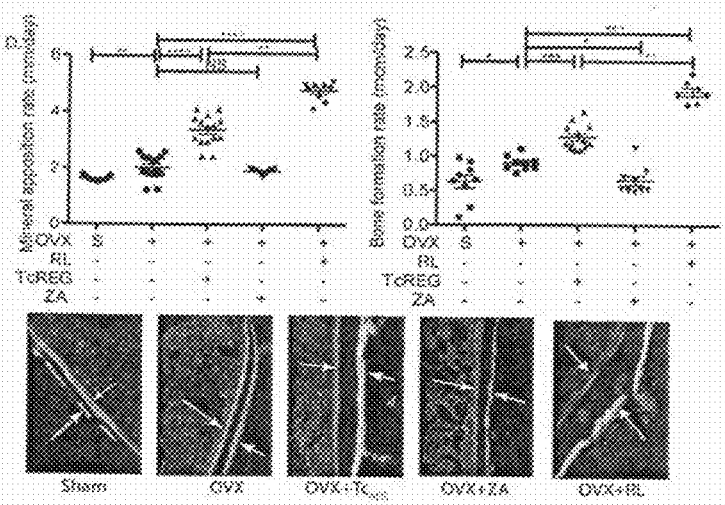

FIGS. 9E-9F provide for examples of a low-dose RANKL treatment in a mouse model All mice (C57BL/6J) were sham-operated (S) or ovariectomized (OVX) at 12 weeks of age. At time indicated after OVX, two doses of RANKL (0.125 mg/kg) were administered 24 hours apart. 10 days after first treatment, mice were sacrificed. As shown in FIGS. 9A and 9B Low-dose RANKL induced $Tc_{REG}$, and decreased proinflammatory effector cells in the femora measured using flow-cytometry. A shown in FIG. 9C, treatment decreased serum CTX levels (blood obtained via mandible vein prior to sacrifice) and, as shown in FIG. 9D increased bone mass of the proximal tibia as measured by μCT. Representative images of the proximal tibia are shown from 3 weeks post-OVX in FIG. 9E. Dynamic histomorphometry as provided in FIG. 9F showed that RANKL treatment increased mineral apposition (left panel) and bone formation rate (right). Representative images from the double-labeled femur (calcein green and alizarin red) from each group are shown. Arrows are shown to emphasize the distance between dyes. Data from 6 to 12 mice per group. For figure reference: **=$P<1\times10^{-4}$; *=$P<1\times10^{-3}$; **=$P<0.01$; *=$P<0.05$ and NS=not statistically significant.

Figure 10D:
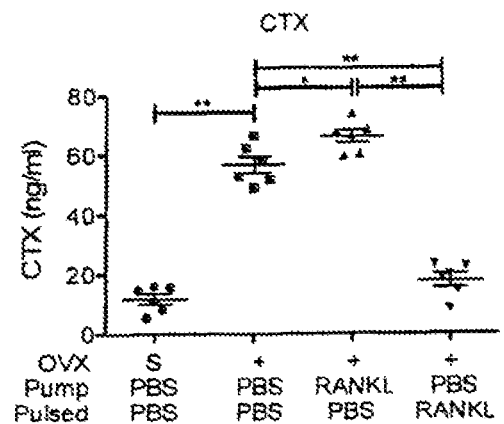
Figure 10E:
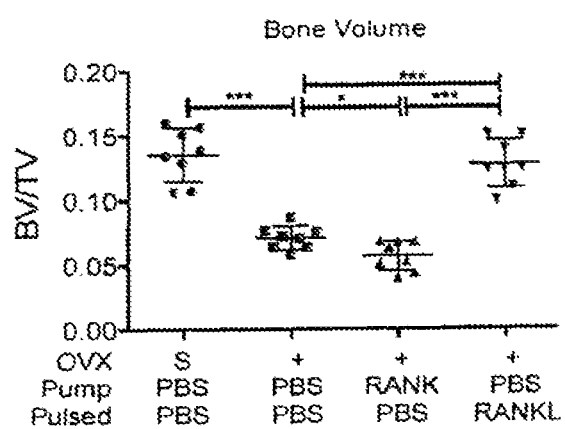

FIGS. 10A through 10E show the effect of delivering RANKL in pulses as opposed to a continuous exposure leads to its antiresorptive effect. 12-week old mice were treated either as sham-operated or OVX using pumps or pulsed. Two weeks post-surgery ALZET® pumps were implanted in the intraperitoneal cavity that contained either PBS or RANKL as indicated in the plots above. All groups were pulsed with equivalent dose of RANKL (0.125 mg/kg, pulsed twice 24 hrs. apart) or PBS as indicated in the plots. In FIG. 10A, the data shows that pulsed but not continuous exposure to RANKL induced $Tc_{REG}$. In FIG. 10B, Quantification across groups (6 mice/group). In FIG. 10C consistent with TcREG induction, decrease in TEFF cells was only observed in mice pulsed with RANKL, but not with pumps. In FIG. 10D decreased levels of bone resorption were observed in mice pulsed with low-dose RANKL but not in mice with continuous exposure to RANKL. In FIG. 10E, Bone volume (BV/TV) decreased in mice where RANKL was delivered by pump, but restored to levels observed in sham-operated mice when pulsed with RANKL.

To assess the kinetics of a single treatment, C57BL/6J ovariectomized mice were treated with low-dose RANKL (administered twice 24 hrs apart, 2 weeks post-OVX) and then followed by serum CTX assay. As shown in FIG. 11A, the results indicate that single treatment is effective to limit bone loss for up to 30 days. In FIG. 11B, to assess whether multiple treatments are effective, sham-operated (S×) or OVX 12-week old C57BL/6J mice were treated with low-dose RANKL (0.125 mg/kg) once per month or once with the bisphosphonate Zoledronate (ZA; 3 weeks post-OVX). 120 days post-OVX peripheral blood obtained by mandible bleeds was treated to remove RBCs (BD Pharmalyse) then 1 to 3×10⁶ cells were plated per well in triplicate (6 mice/group). Media was collected after 36 hours of culturing and cytokine levels quantitated by multiplexed ELISA (Millipore). Of the six cytokines (IFNγ, IL1β, IL4, IL6, TNFα and IL17A) measured, TNFα and IL17A were found to be elevated. **P≤0.01. These results demonstrate systemic circulation of cells that produce these proinflammatory cytokines post menopause consistent with human studies. Low-dose RANKL treatment, but not ZA was immunosuppressive.

FIGS. 12A through 12B indicate whether suppressing bone resorption using Cathepsin K inhibitor, Odanacatib (ODN), would affect induction of TcREG by low-dose RANKL. In FIG. 12A, in culture, bone marrow cell-derived osteoclasts are able to induce FoxP3 in OVA-specific OT-I CD8 T-cells when pulsed with peptide antigen (SIINFEKL). This induction was not affected by Odancatib. In FIG. 12B, mice were treated with Odanacatib, then low-dose RANKL was administered. In the presence of Odancatib, $Tc_{REG}$ induction was not observed. As Cathepsin K is needed to process and release matrix proteins from bone, we interpret these results that osteoclasts crosspresent antigens derived from the protein matrix (e.g. collagen) to CD8 T-cells to induce FoxP3 in CD8 T-cells.

Based on the above, $Tc_{REG}$ are inducible in OVX mice, regardless of time post-OVX. Induction of $Tc_{REG}$ leads to limiting bone resorption, decreased levels of proinflammatory effector T-cells and increased bone formation and mineralization rates. Given well understood corollaries between mice and humans, this would imply that bone resorption can be similarly reduced in humans as a result of postmenopausal osteoporosis.

The RANKL administration must be pulsed to induce TcREG in OVX mice. No $Tc_{REG}$ induction is observed when RANKL is delivered continuously via osmotic pumps. Continuous delivery of RANKL led to increased bone resorption.

A single treatment of low dose RANKL was effective for approximately 28 days (when administered 2 weeks post-OVX) at limiting bone resorption.

Once-per-month treatments were effective at lowering circulating proinflammatory T-cells leading to decreased IL-17A and TNFα in peripheral blood.

Lastly, it appears Cathepsin K inhibitor Odanacatib blocked $Tc_{REG}$ induction in vivo, but not in vitro. Cathepsin K is a protease secreted by osteoclasts that degrades collagen and elastins in the bone. As inhibition of Cathepsin K by Odanacatib blocks $Tc_{REG}$ induction in vivo, without being limited by any particular method of operation, these results are interpreted to indicate that osteoclasts present antigens that are derived from protein matrix in the bone to induce $Tc_{REG}$. Osteoclasts are able to induce $Tc_{REG}$ in vitro, in the presence of the inhibitor indicating that Odanacatib has no direct effect on osteoclasts or T-cells.

T-cells that produce the proinflammatory cytokines IL-17A and TNFα increased in ovariectomized mice, and these T-cells could be detected in peripheral blood (venous blood obtained by mandible bleeds). There are a number of co-morbidities associated with menopause. As circulating T-cells could produce TNFα and IL-17A, it is believed that some of these co-morbidities may be caused by T-cells that are activated in the bone marrow, where memory T-cells reside, and once activated they cause osteoporosis, and then are released and promote inflammatory response at other sites.

With specific regards to determining an effect on atherosclerosis, ten-week old female mice that were either C57BL/6J (WT) or lacking low-density lipoprotein receptor (LDLR) were randomly assigned to chow (LabDiet 5L0B, containing 5% fat and 0.014% cholesterol, by weight) or a "Western Diet" that was high in fat and cholesterol (Teklad TD.96121, containing 21% fat and 1.23% cholesterol). When the mice were 12 weeks old, all animals were surgically operated. Half the mice were ovariectomized (simulating menopause), and the other half had sham surgery. One group of ovariectomized mice on the Western Diet were treated with pulsed low dose RANKL (0.125 mg/kg) 14 days post surgery (14 weeks of age) and 6 weeks post surgery (18 weeks old). All mice were sacrificed at 20 weeks of age, and bone loss and aortic plaque development were analyzed.

FIGS. 13A and 13B illustrate that the ovariectomized mice showed increases in inflammation that was reduced by a low-dose RANKL treatment when compared to treatment with Zolendronate, which is commonly used to treat osteoporosis. FIGS. 14A and 14B illustrate that mice treated with low dose RANKL also showed less weight gain than those without treatment. FIGS. 15A and 15B illustrate that plaque volume in low dose treated mice was also reduced. While ovariectomy induced inflammation appears to be insufficient to promote atherogenesis on its own (in the time frame examined), there is a synergy with diet-induced inflammation to promote inflammation and fatty streak formation in the vasculature of the heart and arteries. In combination, the various results show that low-dose RANKL treatment does not only ameliorate osteoporosis in ovariectomized mice that were fed a western diet, but the number of atherosclerotic lesions in the aortic root was reduced when evaluated at completion of the trial.

Pulsed low-dose RANKL therapy ameliorates osteoporosis as shown in U.S. patent application Ser. No. 15/052,793 and also decreases the size of atherosclerotic lesions in the heart. Without being bound to any particular theory of operation, this is believed to occur by lowering the inflammatory burden from menopause and western diet.

Pulsed low-dose RANKL is typically given once per month although in other embodiments, it could be provided at different intervals. However, one benefit of once per month treatment is that this approach generally has a better safety profile than drugs like statins or Pesk9 inhibitors. RANKL treatments involve materials with a typically short half-life and therefore provides limited exposure minimizing non-specific effects and immune responses. Second, the RANKL is administered at a very low dosage, corresponding to the physiological (endogenous) levels of RANKL, thus also minimizing off target effects. Third, RANKL activates osteoclasts to initiate antigen presentation and thus induces $TC_{REG}$. Therefore, RANKL activates a physiological pathway that is specifically immunosuppressive. Finally, RANKL treatment targets the source of inflammation at the source, unlike a systemic inhibitor that competes with endogenous substrates and therefore has to be present at a high dose.

While the invention has been disclosed in connection with certain preferred embodiments, this should not be taken as a limitation to all of the provided details. Modifications and variations of the described embodiments may be made without departing from the spirit and scope of the invention, and other embodiments should be understood to be encompassed in the present disclosure as would be understood by those of ordinary skill in the art.

The invention claimed is:

1. A method for inhibiting atherosclerosis in a patient the method comprising:
   providing said patient a RANK agonist being of:
      sufficient amount to induce osteoclasts of said patient to produce foxP3+ CD8 T-cells (Tc$_{REG}$); and
      insufficient amount to activate enough of said osteoclasts to create new bone loss in said patient;
   repeating said providing according to a fixed schedule so as to provide said RANK agonist to said patient at pulsed intervals, said patient having as a result of said fixed schedule increased bone mass compared to a patient not on said fixed schedule.

2. The method of claim 1, wherein said RANK agonist is RANKL.

3. The method of claim 1, wherein said low dose comprises 0.125 mg/kg RANKL or less.

4. The method of claim 1, wherein said low dose comprises about 0.125 mg/kg RANKL.

5. The method of claim 1, wherein said low dose comprises 0.05 mg/kg RANKL or less.

6. The method of claim 1, wherein said low dose comprises 0.5 mg/kg RANKL or less.

7. The method of claim 1, wherein the pulsed intervals are about once a month.

* * * * *